(12) United States Patent
Sahin et al.

(10) Patent No.: US 9,950,065 B2
(45) Date of Patent: Apr. 24, 2018

(54) PARTICLES COMPRISING A SHELL WITH RNA

(71) Applicants: BIONTECH AG, Mainz (DE); TRON—Translationale Onkologie an der Universitätsmedizin der Johannes Gutenberg-Universität Mainz gemeinnützige GmbH, Mainz (DE); UNIVERSITÄTSMEDIZIN DER JOHANNES GUTENBERG-UNIVERSITÄT MAINZ, Mainz (DE)

(72) Inventors: Ugur Sahin, Mainz (DE); Heinrich Haas, Mainz (DE); Sebastian Kreiter, Mainz (DE); Yves Hüsemann, Wiesbaden (DE); Mustafa Diken, Mainz (DE); Kerstin Reuter, Darmstadt (DE); Hossam Hefresha, Wiesbaden (DE)

(73) Assignees: BIONTECH RNA PHARMACEUTICALS GMBH, Mainz (DE); TRON—TRANSLATIONALE ONKOLOGIE AN DER UNIVERSITATSMEDIZIN DER JOHANNES GUTENBERG-UNIVERSITAT MAINZ GEMEINNUZIGE GMBH, Mainz (DE)

( * ) Notice: Subject to any disclaimer, the term of this patent is extended or adjusted under 35 U.S.C. 154(b) by 0 days.

(21) Appl. No.: 15/023,052

(22) PCT Filed: Sep. 26, 2013

(86) PCT No.: PCT/EP2013/002898
§ 371 (c)(1),
(2) Date: Mar. 18, 2016

(87) PCT Pub. No.: WO2015/043613
PCT Pub. Date: Apr. 2, 2015

(65) Prior Publication Data
US 2016/0250323 A1    Sep. 1, 2016

(51) Int. Cl.
| A61K 39/39 | (2006.01) |
| A61K 39/00 | (2006.01) |
| A61K 9/127 | (2006.01) |
| A61K 9/50 | (2006.01) |
| A61K 31/675 | (2006.01) |
| C12N 15/88 | (2006.01) |

(52) U.S. Cl.
CPC ............ *A61K 39/39* (2013.01); *A61K 9/1271* (2013.01); *A61K 9/1277* (2013.01); *A61K 9/5073* (2013.01); *A61K 31/675* (2013.01); *A61K 39/0011* (2013.01); *C12N 15/88* (2013.01); *A61K 2039/55505* (2013.01); *A61K 2039/55511* (2013.01); *A61K 2039/55516* (2013.01); *A61K 2039/55555* (2013.01); *A61K 2039/55561* (2013.01); *A61K 2039/572* (2013.01); *C12N 2810/10* (2013.01)

(58) Field of Classification Search
None
See application file for complete search history.

(56) References Cited

U.S. PATENT DOCUMENTS

2010/0104622 A1    4/2010    Spanjaard

FOREIGN PATENT DOCUMENTS

| JP | 2009-507029 A | 2/2009 |
| JP | 2013-530245 A | 7/2013 |
| WO | 00/46147 | 8/2000 |
| WO | 2007/028020 A2 | 3/2007 |
| WO | 2009/110939 | 9/2009 |
| WO | 2012/006369 A2 | 1/2012 |

OTHER PUBLICATIONS

Hafeman, et al. (May 18, 2011 online, 2012 print) "Bisphosphonates Significantly Increase the Activity of Doxorubicin or Vincristine Against Canine Malignant Histiocytosis Cells", Veterinary and Comparative Oncology, 10(1): 44-56.*
International Preliminary Report on Patentabiltiy dated Apr. 7, 2016 for International Application No. PCT/EP2013/002898 filed Sep. 26, 2013.
Buyens et al., "A fast and sensitive method for measuring the integrity of siRNA-carrier complexes in full human serum", Journal of Contolled Release, 2008, vol. 126, 67-76.

* cited by examiner

*Primary Examiner* — Robert M Kelly
(74) *Attorney, Agent, or Firm* — McDonnell Boehnen Hulbert & Berghoff LLP

(57) ABSTRACT

The present invention relates to RNA decorated particles such as RNA decorated lipid particles, preferably to RNA decorated liposomes. Further, the present invention relates to a pharmaceutical composition comprising RNA decorated particles such as RNA decorated lipid particles, preferably RNA decorated liposomes. Said pharmaceutical composition is useful for inducing an immune response. It is also useful in a prophylactic and/or therapeutic treatment of a disease involving an antigen. Furthermore, the present invention relates to a method for producing the RNA decorated particles such as RNA decorated lipid particles, preferably RNA decorated liposomes.

20 Claims, 7 Drawing Sheets

PARTICLES COMPRISING A SHELL WITH RNA

TECHNICAL FIELD OF THE INVENTION

The present invention relates to RNA decorated particles such as RNA decorated lipid particles, preferably to RNA decorated liposomes. Further, the present invention relates to a pharmaceutical composition comprising RNA decorated particles such as RNA decorated lipid particles, preferably RNA decorated liposomes. The pharmaceutical composition is useful for inducing or enhancing an immune response. It is also useful in a prophylactic and/or therapeutic treatment of a disease involving an antigen. Furthermore, the present invention relates to a method for producing the RNA decorated particles such as RNA decorated lipid particles, preferably RNA decorated liposomes.

BACKGROUND OF THE INVENTION

Hydrophilic molecules such as nucleic acids or water-soluble drugs are often carried by lipid vesicles providing a protective environment so that said molecules can cross cell membranes and enter target cells. Lipid vesicles are substantially spherical structures made of materials having a high amphiphilic lipid content. Lipid vesicles are usually called liposomes, if the lipid molecules are orientated in a lipid bilayer around an aqueous cave. Hydrophilic molecules but also hydrophobic molecules as well as amphiphilic molecules can be carried by liposomes. In particular, hydrophilic molecules can be carried by liposomes being comprised in the aqueous internal space of the liposomes, hydrophobic molecules can be carried by liposomes being comprised in the lipid bilayer of the liposomes and amphiphilic molecules can be carried by liposomes being comprised at the interface between lipid bilayer and aqueous internal space of the liposomes. Liposomes can be distinguished by their form and size and can be classified, for example, in multilamellar vesicles (MLV), large unilamellar vesicles (LUV), small unilamellar vesicles (SUV) or in other forms.

In the last decades, a wide range of liposome formulations have been investigated for use in medical applications, cosmetics or food industry. The first most prominent liposome-based products are the cancer drugs Doxil (Sequus) and DaunoXome (Gilead, Nexstar), which have been approved by the US Food and Drug Administration (FDA) in the 1990s (Wagner, A., Vorauer-Uhl, K., (2011), Journal of Drug Delivery, 2011:591325). Recent investigations resulted in the generation of new classes of liposomes such as dendrosomes (Sarbolouki, M. N., Sadeghizadeh, M., Yaghoobi, M. M., Karami, A., Lohrasbi, T. (2000), Journal of Chemical Technology and Biotechnology, 75, 919-922) or cationic liposomes (Audouy, S., Hoekstra, D. (2001), Molecular Membrane Biology, 18, 129-143). Cationic liposomes are structures that are made of positively charged lipids and are increasingly being researched for use in gene therapy due to their favourable interactions with negatively charged DNA and cell membranes. Recently, cationic liposomes have been provided not only for carrying DNA molecules but also for carrying RNA molecules or other therapeutically active compounds.

Disadvantages of current liposomes are that they need to be tailored for a given type of compound. For example, lipophilic, hydrophilic or polymeric compounds need different lipidic carriers to obtain suitable payload and targeting efficacy. One problem with water soluble compounds is the susceptibility to leakage, for example on binding to proteins, peptides, polynucleic acids or polymers in general. Thus, there is a need of improved formulations of particles for the delivery of therapeutically active compounds.

As mentioned above, lipid particles, such as liposomes, have usually therapeutic active compounds encapsulated in their interior. The present inventors surprisingly found that with particles having water-soluble compounds encapsulated in their lipid vesicular core RNA can be bound thereon, maintaining the vesicular organization, and maintaining, partially or completely the encapsulated compound. The RNA decoration does not lead to loss of the encapsulated therapeutically active compound. It is known that RNA molecules are easily degraded in body fluids after systemic administration by ribonucleases. The present inventors surprisingly found that the RNA on the RNA decorated particles is stable and does not form aggregates.

SUMMARY OF THE INVENTION

In a first aspect, the present invention relates to a particle comprising:
(i) a vesicular core,
(ii) at least one therapeutically effective compound encapsulated within the vesicular core, and
(iii) RNA forming a hydrophilic shell on at least a portion of the vesicular core.

In one embodiment, the particle has a net negative charge, a net positive charge or is electroneutral.

In one embodiment, the RNA is pharmaceutically active or encodes at least one pharmaceutically active peptide or protein. In one embodiment, the RNA encodes at least one antigen.

In one preferred embodiment, the antigen is a disease-associated antigen or elicits an immune response against a disease-associated antigen or cells expressing a disease-associated antigen.

In one embodiment, the RNA is exposed to surrounding medium.

In one embodiment, the RNA covers the entire surface of the vesicular core or a portion thereof.

In one embodiment, the therapeutically effective compound is a water-soluble compound.

In one embodiment, the therapeutically effective compound is a small molecule compound.

In one embodiment, the therapeutically effective compound is useful in immunotherapy.

In one embodiment, the therapeutically effective compound is an agent stimulating γδ T cells, preferably Vγ9Vδ2 T cells.

In one preferred embodiment, the agent stimulating γδ T cells is a bisphosphonate. In one more preferred embodiment, the agent stimulating γδ T cells is a nitrogen-containing bisphosphonate (aminobisphosphonate). In one even more preferred embodiment, the agent stimulating γδ T cells is selected from the group consisting of zoledronic acid, clodronic acid, ibandronic acid, pamidronic acid, risedronic acid, minodronic acid, olpadronic acid, alendronic acid, incadronic acid and salts thereof.

In one embodiment, the vesicular core is positively charged.

In one embodiment, the vesicular core is a polymer vesicular core, a protein vesicular core or a lipid vesicular core, preferably a lipid vesicular core.

In one particularly preferred embodiment, the invention relates to particle comprising:

(i) a positively charged lipid vesicular core,
(ii) at least one therapeutically effective compound encapsulated within the vesicular core, and
(iii) RNA forming a hydrophilic shell on at least a portion of the vesicular core.

In one embodiment, the lipid vesicular core comprises a lipid bilayer.

In one embodiment, the lipid vesicular core comprises a liposome.

In one embodiment, the lipid vesicular core comprises at least one cationic lipid.

In one preferred embodiment, the lipid vesicular core comprises a liposome comprising at least one cationic lipid.

In one embodiment, the positive charges are contributed by the at least one cationic lipid and the negative charges are contributed by the RNA.

In one embodiment, the lipid vesicular core comprises at least one helper lipid.

In one preferred embodiment, the helper lipid is a neutral lipid or negatively charged lipid.

In one preferred embodiment, the at least one cationic lipid comprises 1,2-dimyristoyl-sn-glycero-3-ethylphosphocholine (DMEPC), 1,2-di-O-octadecenyl-3-trimethylammonium propane (DOTMA) and/or 1,2-dioleoyl-3-trimethylammonium propane (DOTAP). In one more preferred embodiment, the at least one cationic lipid comprises DMEPC and/or DOTMA.

In one preferred embodiment, the at least one helper lipid comprises 1,2-distearoyl-sn-glycero-3-phosphocholine (DSPC), 1,2-di-(9Z-octadecenoyl)-sn-glycero-3-phosphoethanolamine (DOPE), cholesterol (Chol), 1-palmitoyl-2-oleoyl-sn-glycero-3phosphocholin (POPC) and/or 1,2-dioleoyl-sn-glycero-3-phosphocholine (DOPC). In one more preferred embodiment, the at least one helper lipid comprises DSPC, DOPE, and/or Chol.

In one even more preferred embodiment, the at least one cationic lipid comprises DMEPC and the at least one helper lipid comprises DSPC and DOPE, or the at least one cationic lipid comprises DOTMA and the at least one helper lipid comprises Chol.

In one embodiment the particle has an average diameter in the range of from about 50 nm to about 1000 nm. In one embodiment the particle has an average diameter in the range of from about 300 nm to about 600 nm. In one embodiment the particle has an average diameter of about 200 nm or less. Particles having an average diameter in the range of from about 300 nm to about 600 nm are preferably useful for targeting antigen presenting cells, preferably antigen presenting cells in the spleen, preferably professional antigen presenting cells such as dendritic cells. Particles having an average diameter of about 200 nm or less are preferably useful for targeting tumor cells.

In one preferred embodiment, the particle has an average diameter
(i) in the range of from about 50 nm to about 400 nm, preferably from about 50 nm to 200 nm, or
(ii) in the range of from about 200 nm to about 1000 nm, preferably from about 200 nm to about 800 nm, more preferably from about 300 nm to about 600 nm.

In one embodiment, the lipid vesicular core having the therapeutically effective compound encapsulated therein is obtainable by reverse phase evaporation technique or ethanol injection technique.

In one embodiment, the particle is obtainable by addition of the RNA to a lipid vesicular core having the therapeutically effective compound encapsulated therein.

In one embodiment, the particle is obtainable by a process comprising a step of extruding and/or a step of lyophilizing the particle.

In a second aspect, the present invention relates to a pharmaceutical composition comprising particles according to the first aspect.

In one embodiment, after systemic administration of the particles, at least a portion of the RNA and at least a portion of the therapeutically effective compound are delivered to a target cell, preferably to the same target cell. In one embodiment, the target cell is a spleen cell, preferably an antigen presenting cell, more preferably a professional antigen presenting cell, more preferably a dendritic cell. Thus, particles of the invention may be used for delivering RNA and a therapeutically effective compound to such target cell.

In one embodiment, after systemic administration of the particles, RNA accumulation and/or RNA expression in the spleen occurs. Thus, particles of the invention may be used for expressing RNA in the spleen.

In one embodiment, after systemic administration of the particles, no or essentially no RNA accumulation and/or RNA expression in the lung and/or liver occurs.

In one embodiment, after systemic administration of the particles, RNA accumulation and/or RNA expression in the spleen is at least 5-fold the amount of RNA accumulation and/or RNA expression in the lung.

In one embodiment, after systemic administration of the particles, RNA accumulation and/or RNA expression in antigen presenting cells, preferably professional antigen presenting cells, in the spleen occurs. Thus, particles of the invention may be used for expressing RNA in such antigen presenting cells.

In one preferred embodiment, the antigen presenting cells are dendritic cells and/or macrophages.

In one embodiment, systemic administration is by parenteral administration, preferably by intravenous administration, subcutaneous administration, intradermal administration or intraarterial administration.

In one embodiment, the pharmaceutical composition further comprises one or more pharmaceutically acceptable carriers, diluents, and/or excipients.

In one embodiment, the pharmaceutical composition further comprises at least one adjuvant.

In one embodiment, the pharmaceutical composition is formulated for systemic administration.

In a third aspect, the present invention relates to the pharmaceutical composition according to the second aspect for inducing or enhancing an immune response, preferably an immune response against cancer.

In a fourth aspect, the present invention relates to the pharmaceutical composition according to the second aspect, for use in a prophylactic and/or therapeutic treatment of a disease involving an antigen, preferably a cancer disease.

In a fifth aspect, the present invention relates to a method for delivering an antigen to antigen presenting cells, preferably professional antigen presenting cells, in the spleen or expressing an antigen in antigen presenting cells, preferably professional antigen presenting cells, in the spleen
comprising administering to a subject a pharmaceutical composition according to the second aspect. In this aspect, the antigen or a portion thereof is preferably encoded by the RNA forming a hydrophilic shell on at least a portion of the vesicular core.

In one preferred embodiment, the antigen presenting cells are dendritic cells and/or macrophages.

In a sixth aspect, the present invention relates to a method for inducing or enhancing an immune response, preferably an immune response against cancer, in a subject comprising administering to the subject a pharmaceutical composition according to the second aspect.

In a seventh aspect, the present invention relates to a method for stimulating, priming and/or expanding T cells in a subject comprising administering to the subject a pharmaceutical composition according to the second aspect.

In an eighth aspect, the present invention relates to a method of treating or preventing a disease involving an antigen, preferably a cancer disease, in a subject comprising administering to the subject a pharmaceutical composition according to the second aspect. In this aspect, the antigen or a portion thereof is preferably encoded by the RNA forming a hydrophilic shell on at least a portion of the vesicular core.

In a ninth aspect, the present invention relates to a method of producing a particle according to the first aspect comprising the following steps of:
(i) providing a vesicular core having at least one therapeutically effective compound encapsulated therein, and
(ii) adding RNA to the vesicular core, wherein the RNA forms a hydrophilic shell on at least a portion of the vesicular core, thereby forming the particle.

Embodiments of the vesicular core, the therapeutically effective compound, the RNA and/or the particle produced are as described above.

In one embodiment, the vesicular core is a lipid vesicular core, preferably a positively charged lipid vesicular core.

In one preferred embodiment, the lipid vesicular core to which the RNA is added comprises a liposome comprising at least one cationic lipid.

In one preferred embodiment, the amount of RNA and the amount of cationic lipids in the liposome is selected such that the net charge formed by the positive charges derived from the cationic lipids and the negative charges derived from the RNA is negative, positive, or zero.

In one even more preferred embodiment, the number of positive charges derived from the cationic lipids divided by the number of negative charges derived from the RNA is between 0.025 and 4, preferably is 0.025, 0.125, 0.250, 0.375, 0.500, 0.625, 0.750, 0.875, 1, 2, 3, or 4.

This summary of the invention does not necessarily describe all features of the invention.

Zoledronic acid (ZA) encapsulating liposomes (ZA liposomes) with different compositions and molar fractions of the cationic lipid DOTMA were prepared and the binding of RNA to these liposomes was investigated. The liposome composition was as follows: DOTMA/CHOL/POPC 10/50/40, DOTMA/CHOL/POPC 20/50/30, DOTMA/CHOL/POPC 30/50/20, DOTMA/CHOL/POPC 40/50/10, and DOTMA/CHOL/POPC 50/50/0 molar ratio, respectively. Thus, the liposomes were composed of 10%, 20%, 30%, 40%, or 50% DOTMA. Binding was investigated by adding an excess of RNA to the zoledronic acid (ZA) encapsulating liposomes (ZA liposomes) and quantifying the RNA by capillary electrophoresis (Bioanalyzer). The DOTMA/RNA charge ratios were as follows: DOTMA/RNA (mole/base) =0.025, 0.125, 0.25, 0.375, 0.50, 0.625, 0.75, 0.875, 1.00. When cationic liposomes were present, the measured amount of RNA decreased. The missing RNA was taken as liposome bound RNA. As can be seen, the amount of bound RNA was directly proportional to the amount of DOTMA present in a one-to-one stoichiometry with respect to the charge. This means, for all tested liposomes, that the amount of bound RNA was directly correlated with the amount of DOTMA in the membrane. As the molar fraction of DOTMA changed (from 10% to 50%), also the amount of bound RNA per liposome and the surface coverage of the liposomes with RNA changed. Thus, in the given experiment, RNA covered liposomes, where the surface coverage with RNA changed by a factor of five, could be assembled in a controlled way.

Figure 2:
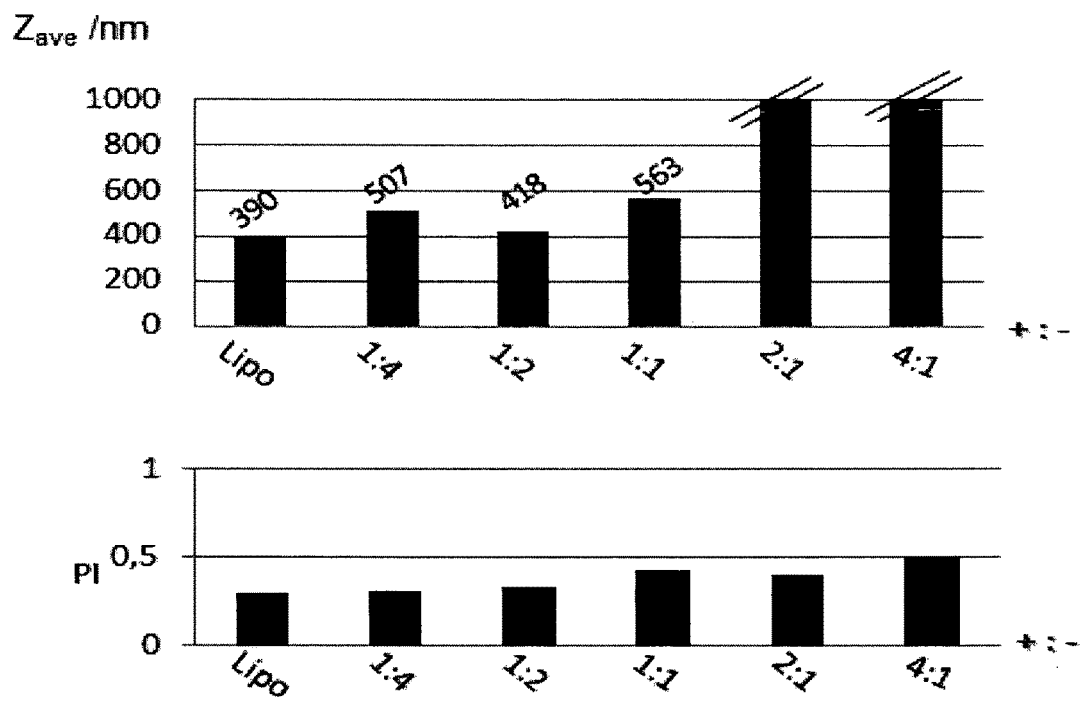

FIG. 2: Particle sizes and polydispersity indices (PI) of cationic ZA-liposomes after addition of RNA at different charge ratios: cationic lipid (DOTMA)/RNA.

The particle sizes and the polydispersity indices (PIs) of different RNA decorated ZA-liposomes (ZARNAsomes) (i.e. RNA decorated zoledronic acid (ZA) encapsulating liposomes) and undecorated ZA-liposomes (i.e. zoledronic acid (ZA) encapsulating liposomes) were compared. The liposomes had the following composition: DOTMA/CHOL/POPC in a 30/50/20 molar ratio. An excess of negative charges and an excess of positive charges was investigated. DOTMA to RNA in a 1/4, 1/2, 1/1, 2/1, and 4/1 positive charge/negative charge-ratio (+/−) were tested. The sizes, indicated in Z-averages ($Z_{ave}$), and the polydispersity indices (PIs) of the particles were measured by Photon Correlation Spectroscopy. As can be seen, in case of an excess of negative charges (charge reversal with respect to the precursor cationic liposomes), liposome formulations with discrete particle sizes were obtained, and no aggregation was observed. Only moderate changes of the particle size with respect to the precursor liposomes occurred, that may be in line with the bound molecular layer on the liposome surface.

Figure 3:
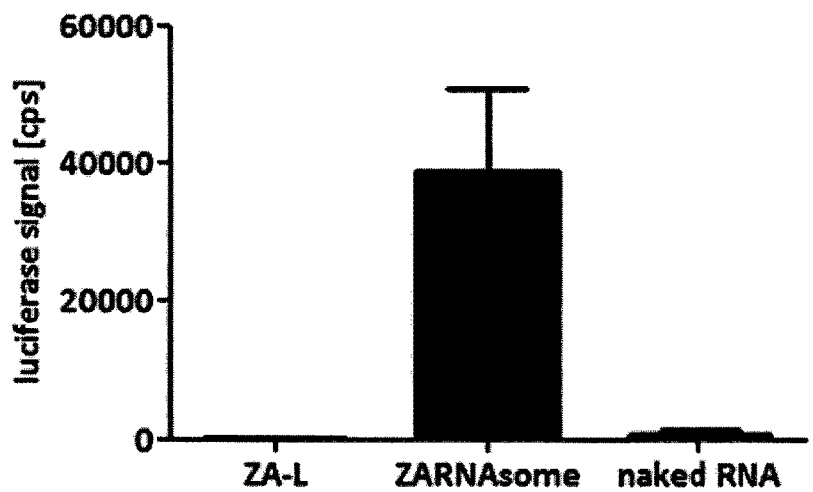

FIG. 3: Expression of luciferase (Luc) in vitro transcribed (IVT) RNA in dendritic cells after incubation with liposome formulations.

The luciferase expression was evaluated via luminescence indicating the metabolic rate of luciferin as substrate for luciferase in counts per seconds (cps). In total, four donors were tested separately. The mean value is shown including the standard deviation (SD). Only luciferase (Luc) RNA decorated zoledronic acid (ZA) containing liposomes (ZARNAsomes) were stable and resulted in luciferase expression, in contrast to naked RNA or zoledronic acid (ZA) containing liposomes without RNA (ZA-L).

Figure 4:
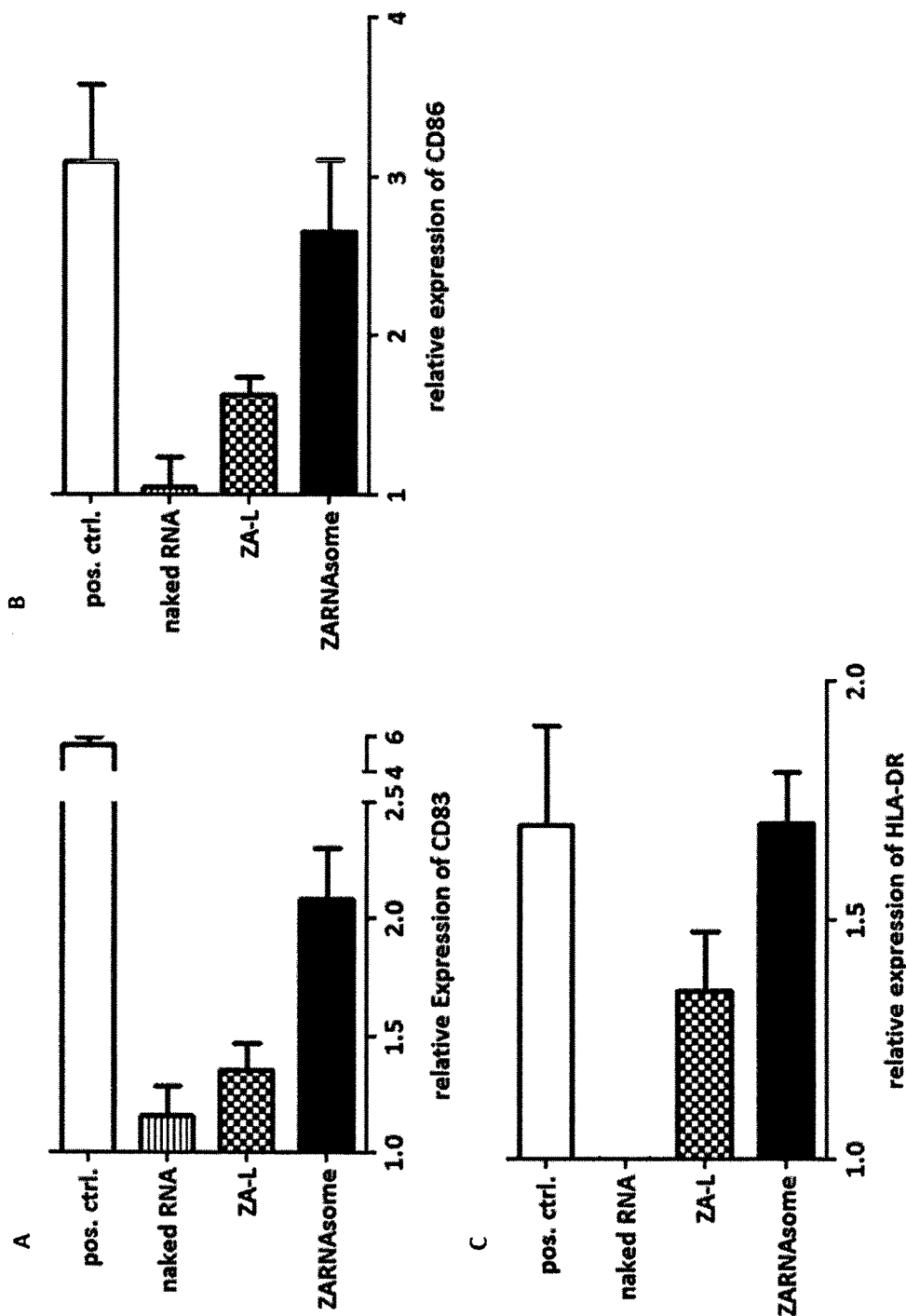

FIG. 4: Relative expression of maturation markers in dendritic cells after incubation with liposome formulations.

Here, the relative expression of CD83 (A), CD86 (B) and HLA-DR (C) is shown. Expression data were normalized to no stimulation control. ZARNAsomes resulted in a distinct higher expression of all markers. Regarding CD86 and HLA-DR, the expression was even comparable with the positive control (pos. ctrl.). Mean values of two donors are shown.

Figure 5:
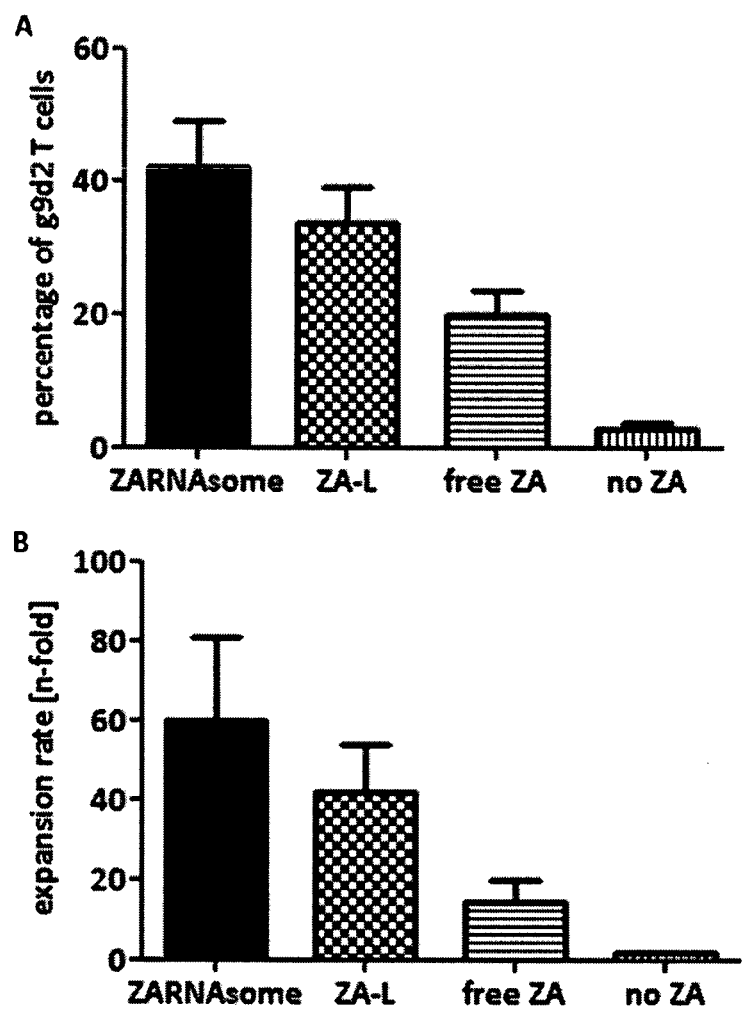

FIG. 5: Functionality of encapsulated zoledronic acid (ZA) after co-cultivation of immature dendritic cells (iDCs) incubated with liposome formulations and peripheral blood lymphocytes (PBLs).

(A) The frequency of Vγ9Vδ2 T cells regarding all lymphocytes is shown. A mean value of two donors is shown. (B) The expansion rate of Vγ9Vδ2 T cells is shown. Total cell numbers after 7-day cultivation have been divided by ex vivo amounts. Also the mean value of two donors is shown. Vγ9Vδ2 T cell frequency and expansion rate was increased in the presence of ZARNAsomes.

Figure 6:
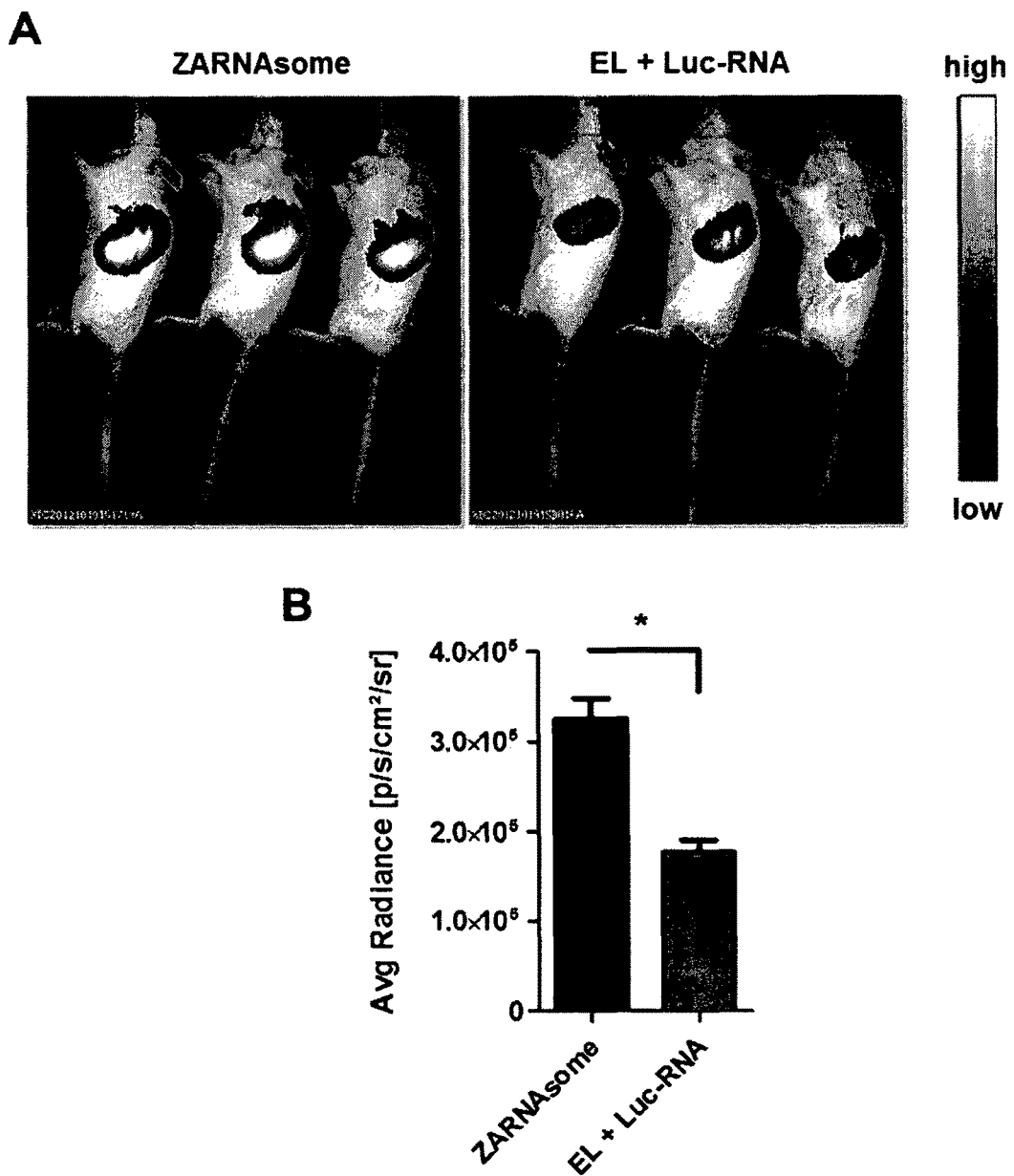

FIG. 6: Application of ZARNAsomes resulted in luciferase expression in the spleen.

Comparison of luciferase (Luc) RNA decorated zoledronic acid (ZA) encapsulating liposomes (ZARNAsomes) with luciferase (Luc) RNA decorated buffer vehicle encapsulating liposomes (EL+Luc-RNA) shows that zoledronic acid (ZA) encapsulation does not negatively influence RNA uptake and translation. The liposomes had the following composition: DOTMA/Chol. (A) Bioluminescence imaging of mice 6 hours after i.v. injection of luciferase (Luc) RNA decorated zoledronic acid (ZA) encapsulating liposomes (Luc-RNA, 20 μg) (ZARNAsomes) or luciferase (Luc) RNA decorated buffer vehicle encapsulating liposomes (Luc-RNA, 20 μg) (EL+Luc-RNA). (B) Quantification of in vivo spleen bioluminescence signal (p/s, photons per second); *$p<0.05$ (t-test).

Figure 7:
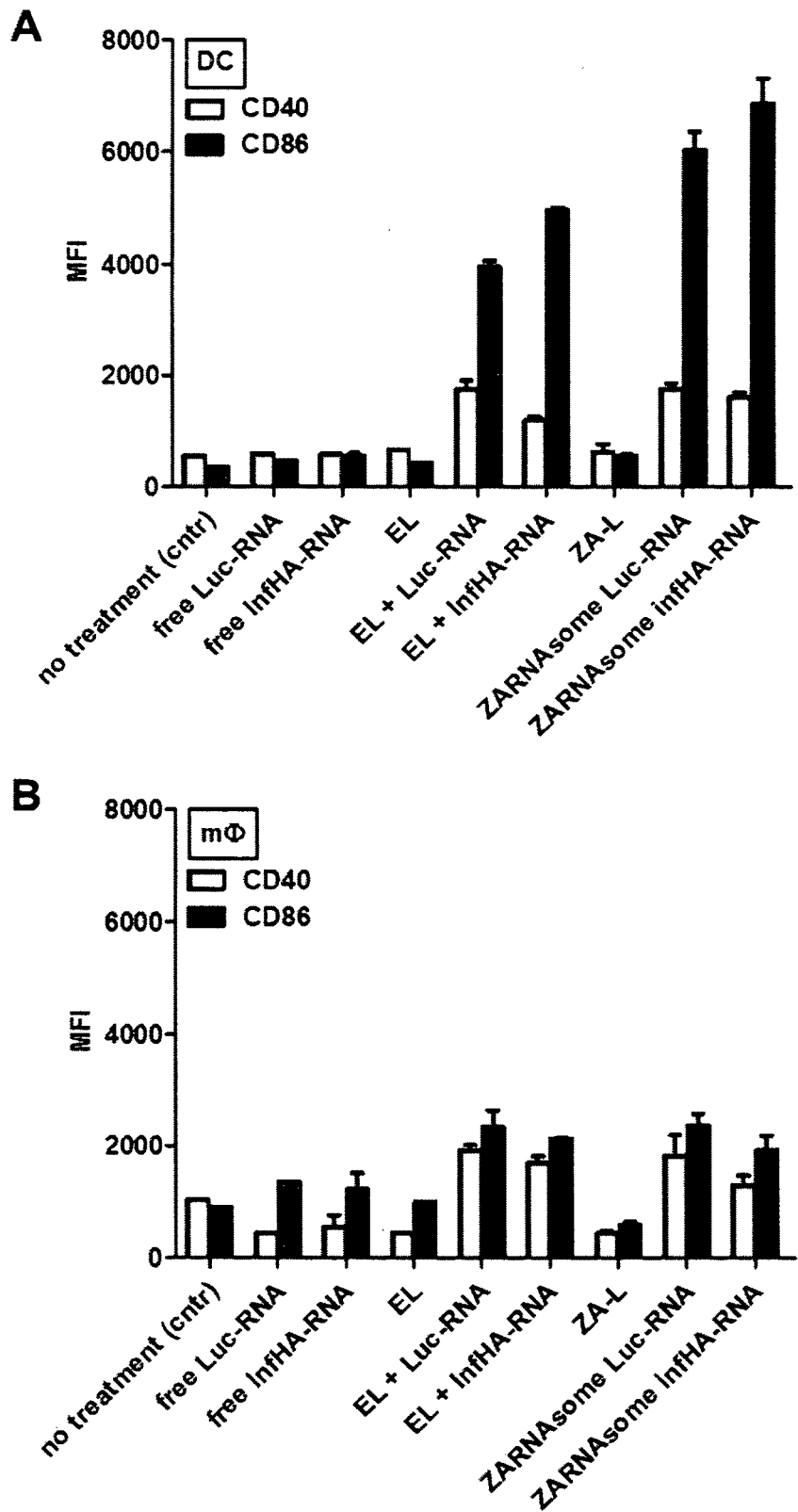

FIG. 7: Application of ZARNAsomes resulted in upregulation of CD40 and CD86 expression on splenic dentritic cells (DCs) and macrophage (mΦ) cell population.

Independent of which antigen the decorated RNA codes for, macrophage and DC maturation was induced in the presence of ZARNAsomes or buffer vehicle encapsulating liposomes decorated with RNA (EL+respective RNA). In contrast thereto, undecorated ZA encapsulating liposomes (ZA-L), buffer vehicle encapsulating liposomes (EL) and free RNA did not lead to macrophage and DC maturation. FACS analysis results of (A) DC-population and (B) macrophage-population of splenocytes 24 hours after i.v. injection of luciferase RNA or influenza hemagglutinin (infHA) RNA (20 μg) decorated ZA encapsulating liposomes (ZARNAsome Luc-RNA, ZARNAsome infHA-RNA), luciferase RNA or influenzaHA RNA (20 μg) decorated buffer vehicle encapsulating liposomes (EL+Luc-RNA, EL+infHA-RNA), buffer vehicle encapsulating liposomes (EL), and free luciferase RNA or influenzaHA RNA (free Luc-RNA or free infHA-RNA) are shown. Mean fluorescence intensities (MFI) of n=1-3 animals are presented. infHA-RNA or InfluenzaHA-RNA=influenza hemagglutinin A RNA.

Figure 8:
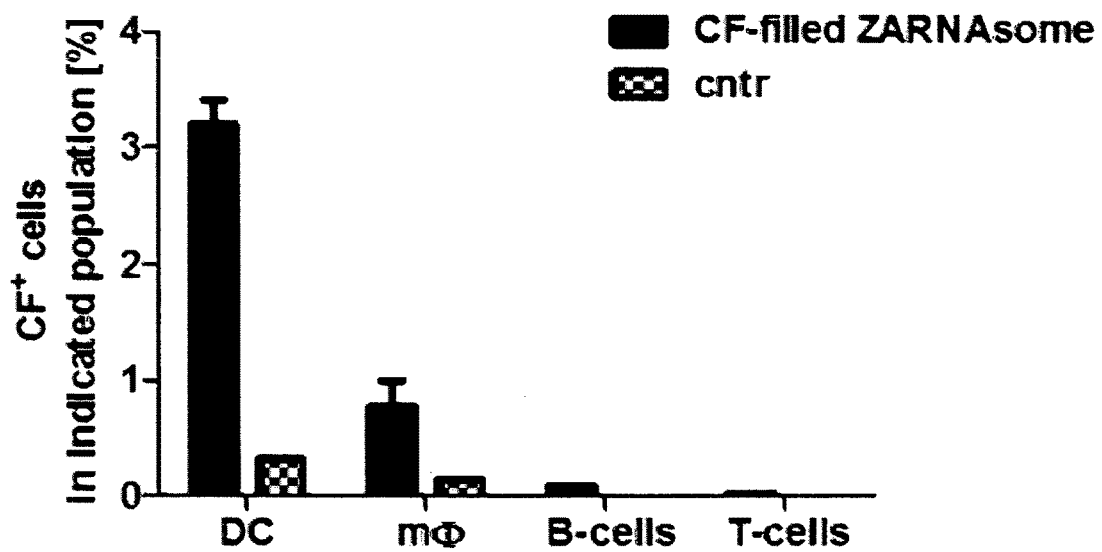

FIG. 8: Application of carboxyfluorescin (CF)-filled liposomes decorated with Luc-RNA (CF-filled ZARNAsome) resulted in transfection of splenic cell populations, whereby dendritic cells (DCs) and macrophages (m4)) were the main targets.

FACS analysis of splenocytes 1 hour after i.v. injection of CF-filled ZARNAsomes complexed with Luc-RNA (20 μg) (CF filled ZARNAsome) showed a CF-signal increase, preferably in dendritic cells and macrophages. Displayed is the frequency of CF positive cells in % of parent population of n=1-3 animals.

Figure 9:
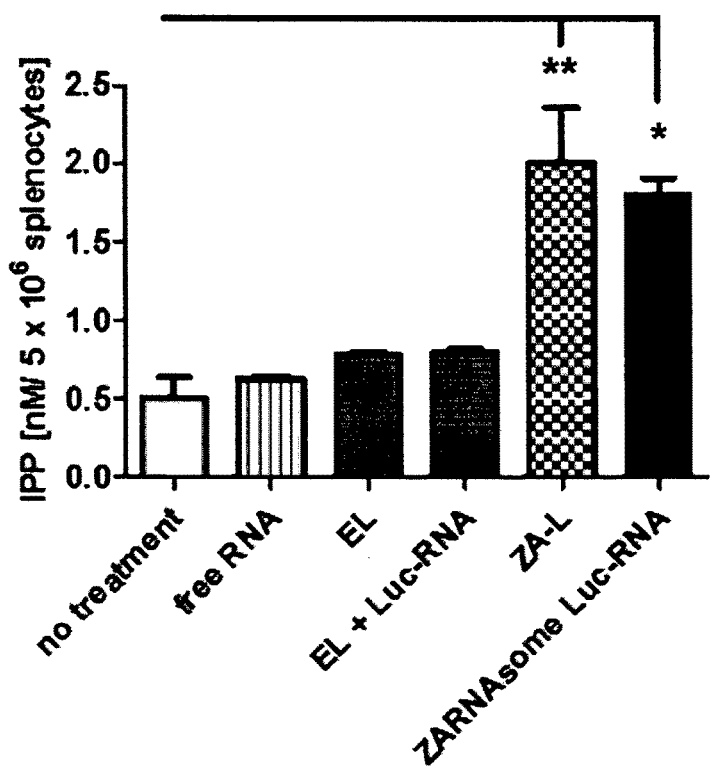

FIG. 9: Zoledronic acid resulted in an accumulation of isopentenylpyrophosphate (IPP) in the spleen.

Application of zoledronic acid (ZA) encapsulating liposomes (ZA-L) and luciferase (Luc) RNA decorated zoledronic acid (ZA) encapsulating liposomes (ZARNAsome Luc-RNA) resulted in an accumulation of Isopentenylpyrophosphate (IPP) in splenocytes. In contrast thereto, application of free luciferase (Luc) RNA (free RNA), buffer vehicle encapsulating liposomes decorated with luciferase (Luc) RNA (EL+Luc RNA) and buffer vehicle encapsulating liposomes (EL) did not increase IPP values. Bars represent mean IPP values of 3 animals 24 h after i.v. administration, *$p<0.05$; **$p<0.01$.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment the particle of the present invention comprises a water-soluble therapeutically effective compound and if in another preferred embodiment the particle of the present invention comprises RNA encoding at least one antigen, it is a contemplated preferred embodiment that the particle of the present invention comprises a water-soluble therapeutically effective compound and RNA encoding at least one antigen.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In the following, definitions will be provided which apply to all aspects of the present invention.

In the context of the present invention, the term "particle" relates to a structured entity formed by molecules or a molecule complex. In one embodiment, the structured entity formed by molecules or a molecule complex comprises a positively charged lipid vesicular core, a therapeutically effective compound encapsulated within the vesicular core, and RNA forming a hydrophilic shell on at least a portion of the vesicular core. The term "particle" in particular relates to a micro- or nano-sized spherical structure.

In one embodiment, the particles of the present invention have an average diameter in the range of from about 50 nm to about 1000 nm, e.g. from about 100 nm to about 900 nm, from about 200 nm to about 800 nm, from about 200 to about 700 nm, from about 300 to about 600 nm, from about 300 nm to about 500 nm, or from about 300 nm to about 400 nm.

In one embodiment, the particles of the present invention have an average diameter of at least about 50 nm, at least about 60 nm, at least about 70 nm, at least about 80 nm, at least about 90 nm, at least about 100 nm, at least about 150 nm, at least about 200 nm, at least about 250 nm, at least about 300 nm, at least about 400 nm, at least about 500 nm, at least about 600 nm, at least about 700 nm, at least about 800 nm, at least about 900 nm, and/or the particles of the present invention have an average diameter of no more than about 1000 nm, no more than about 900 nm, no more than about 800 nm, no more than about 700 nm, no more than about 600 nm, no more than about 500 nm, no more than about 400 nm, no more than about 300 nm, no more than about 250 nm, no more than about 200 nm, no more than about 150 nm, no more than about 100 nm, no more than about 90 nm, no more than about 80 nm, no more than about 70 nm, no more than about 60 nm.

In one preferred embodiment, the particles of the present invention have an average diameter (i) in the range of from about 50 nm to about 400 nm, preferably from about 50 nm to about 200 nm, or (ii) in the range of from about 200 nm to about 1000 nm, preferably from about 200 nm to about 800 nm, more preferably from about 300 nm to about 600 nm. The use of particles having diameters≤about 200 nm is preferred for targeting tumor cells. In addition, the use of particles having diameters between about 300 nm and about 600 nm is preferred for targeting antigen presenting cells such as dendritic cells or macrophages.

In one embodiment, the particles of the present invention are comprised in a formulation such a liquid formulation. Thus, the present invention may refer to a formulation such as a liquid formulation comprising the particles of the present invention.

The term "vesicular core" refers to a vesicle structure capable of encapsulating a therapeutically effective compound and capable of providing a binding surface on its outside for RNA. In other words, the outside of the vesicular core is structured such that it can be covered by RNA and the inside of the vesicular core is structured such that it faces a lumen, in which a therapeutically effective compound can be encapsulated. The vesicular core may be a structure comprising or consisting of and preferably formed by polymers, proteins and/or lipids.

The term "lipid vesicular core" refers to a lipid vesicle structure capable of encapsulating a therapeutically effective compound and capable of providing a binding surface on its outside for RNA. In other words, the outside of the lipid vesicular core is structured such that it can be covered by RNA and the inside of the lipid vesicular core is structured such that it faces a lumen, in which a therapeutically effective compound can be encapsulated. Lipid vesicle structures are substantially spherical structures usually made of materials having high amphiphilic lipid content. The lipids of these spherical vesicles are preferably organized in a lipid layer, more preferably in lipid bilayers, which encapsulate a volume, preferably an aqueous volume. This volume provides a lumen, in which a therapeutically effective compound (e.g. water soluble compound) can be encapsulated. A therapeutically effective compound (e.g. water insoluble compound) can also be comprised in the lipid layer, particularly lipid bilayers, of said spherical vesicles, or a therapeutically effective compound (e.g. amphiphilic compound) can be comprised at the interface between the lipid layer, particularly lipid bilayers, and the encapsulated volume, preferably aqueous volume, of said spherical vesicles.

The term "positively charged lipid vesicular core" means that the net charge of the lipid vesicular core is positive. It is preferred that the lipids forming the lipid vesicular core comprise at least one cationic lipid.

The term "encapsulated" in the expression "a therapeutically effective compound encapsulated within the vesicular core" refers to the position of the therapeutically effective compound in the particle and means that the therapeutically effective compound is comprised in the vesicular core, particularly covered by the vesicular core. For example, the therapeutically effective compound (e.g. water soluble compound) can be comprised in the encapsulated volume, preferably aqueous volume, of the vesicular core, the therapeutically effective compound (e.g. water insoluble compound) can be comprised in a lipid layer, particularly lipid bilayers, of the vesicular core, or the therapeutically effective compound (e.g. amphiphilic compound) can be comprised at the interface between a lipid layer, particularly lipid bilayers, and the encapsulated volume, preferably aqueous volume, of the vesicular core. In all cases, the therapeutically effective compound is encapsulated within the vesicular core.

According to the present invention, the term "lipid" refers to any fatty acid derivative or other amphiphilic compound which is capable of forming a lipid vesicular core. In particular, the term "lipid" refers to any fatty acid derivative which is capable of forming a bilayer such that a hydrophobic part of the lipid molecule orients toward the bilayer while a hydrophilic part orients toward the aqueous phase. The term "lipid" comprises neutral, anionic or cationic lipids. Lipids preferably comprise a hydrophobic domain with at least one, preferably two, alkyl chains or a cholesterol moiety and a polar headgroup. The alkyl chains of the fatty acids in the hydrophobic domain of the lipid are not limited to a specific length or number of double bonds. Nevertheless, it is preferred that the fatty acid has a length of 10 to 30, preferably 14 to 25 carbon atoms. The lipid may also comprise two different fatty acids.

The lipids may include phospholipids or derivatives thereof, sphingolipids or derivatives thereof, or glycolipids or derivatives thereof. The phospholipids may be glycerophospholipids. Examples of a glycerophospholipid include, without being limited thereto, phosphatidylglycerol (PG) including dimyristoyl phosphatidylglycerol (DMPG); phosphatidylcholine (PC), including egg yolk phosphatidylcholine and dimyristoyl phosphatidylcholine (DMPC); phosphatidic acid (PA), phosphatidylinositol (PI), phosphatidylserine (PS) and sphingomyelin (SM) and derivatives of the same.

The term "cationic lipid" refers to a lipid having a net positive charge. The cationic lipid preferably comprises a cationic, meaning positively charged, headgroup. If the positively charged lipid vesicular core comprises a cationic lipid, the positively charged headgroup may be localized outside and inside of the lipid vesicular core. Thus, the positive charges of the cationic lipids forming the positively charged lipid vesicular core preferably face the RNA and the therapeutically effective compound. The hydrophobic domain of cationic lipids is preferably not different from neutral or anionic lipids. The polar headgroup of the cationic lipids preferably comprises amine derivatives such as primary, secondary, and/or tertiary amines, quaternary ammonium, various combinations of amines, amidinium salts, or guanidine and/or imidazole groups as well as pyridinium, piperizine and amino acid headgroups such as lysine, arginine, ornithine and/or tryptophan. More preferably, the polar headgroup of the cationic lipid comprises amine derivatives. Most preferably, the polar headgroup of the cationic lipid comprises a quaternary ammonium. The headgroup of the cationic lipid may comprise multiple cationic charges. It is preferred, that the headgroup of the cationic lipid comprises one cationic charge. Monocationic lipids include 1,2-dimyristoyl-sn-glycero-3-ethylphosphocholine (DMEPC), 1,2-di-O-octadecenyl-3-trimethylammonium propane (DOTMA) and/or 1,2-dioleoyl-3-trimethylammonium propane (DOTAP), 1,2-dimyristoyl-3-trimethylammonium propane (DMTAP), 2,3-di(tetradecoxy)propyl-(2-hydroxyethyl)-dimethylazanium bromide (DMRIE), didodecyl (dimethyl)azanium bromide (DDAB), 1,2-dioleyloxypropyl-3-dimethyl-hydroxyethyl ammonium bromide (DORIE) or 3β-[N—(N\N'-dimethylamino-ethane) carbamoyl]cholesterol (DC-Chol), but are not limited thereto. The cationic lipids may be used alone or in combination with cholesterol, with neutral phospholipids or other known lipid assembly components. The positively charged lipid vesicular core may also include other components typically used in the formation of vesicles (e.g. for stabilization). Examples of such other components includes, without being limited thereto, fatty alcohols, fatty acids, and/or cholesterol esters or any other pharmaceutically acceptable excipients which may affect the surface charge, the membrane fluidity and assist in the incorporation of the lipid into the lipid assembly. Examples of sterols include cholesterol, cholesteryl hemisuccinate, cholesteryl sulfate, or any other derivatives of cholesterol. Preferably, the at least one cationic lipid comprises DMEPC and/or DOTMA.

It is preferred that the portion of the at least one cationic lipid in the lipid vesicular core of the particles of the present invention amounts to at least about 10%, at least about 20%, at least about 30%, at least about 40%, at least about 50%, at least about 60%, at least about 70%, at least about 80%, at least about 90%, or 100%. For example, the portion of DOTMA in the lipid vesicular core of the particles of the present invention may amount to about 10%, about 20%, about 30%, about 40%, or about 50%.

The term "lipid bilayer" refers to a double layer structure of lipids. The term encompasses bilayers of all geometries including but not limited to planar, curved or spherical bilayers. Preferably, the positively charged lipid vesicular core comprises a lipid bilayer.

The term "liposome" refers to a vesicle comprising a lipid bilayer membrane. Liposomes comprise a liquid inner volume, preferably an aqueous inner volume. The lipid membrane of the liposome may comprise components such as, but not limited to, fats, oils, waxes, cholesterol, sterols, monoglycerides, diglycerides, phospholipids, glycolipids, steroids, proteins, and other membrane-associated components. Preferably, the lipid vesicular core such as the positively charged lipid vesicular core is a liposome.

When the lipid vesicular core is a liposome, the liposome may be in the form of multilamellar vesicles (MLV), large unilamellar vesicles (LUV), small unilamellar vesicles (SUV) or multivesicular vesicles (MW) as well as in other bilayered forms known in the art. The size and lamellarity of the liposome will depend on the manner of preparation and the selection of the type of vesicles to be used will depend on the preferred mode of administration. For systemic therapeutic purposes, liposomes having a diameter of between 50 and 150 nm are preferred (LUV or SUV). For local treatment, liposomes having larger diameters, such as MLV or MW, can be used.

The liposome may be further modified, for example, by an antibody, preferably recognizing an antigen specifically expressed on the target cell structure and thereby improving the targeting of the liposome. The liposome is preferably suitable for transporting negatively charged molecules and for transfecting animal cells, preferably mammalian cells, most preferably human cells.

The term "helper lipid" refers to a lipid capable of increasing the effectiveness of delivery of lipid-based particles such as cationic lipid-based particles to a target, preferably into a cell. The helper lipid can be neutral, positively charged, or negatively charged. Preferably, the helper lipid is neutral or negatively charged. Examples for helper lipids include 1,2-distearoyl-sn-glycero-3-phosphocholine (DSPC), 1,2-di-(9Z-octadecenoyl)-sn-glycero-3-phosphoethanolamine (DOPE), cholesterol (Chol), 1-palmitoyl-2-oleoyl-sn-glycero-3phosphocholin (POPC) and 1,2-dioleoyl-sn-glycero-3-phosphocholine (DOPC), but are not limited thereto. Preferably, the at least one helper lipid comprises DSPC, DOPE, and/or Chol.

In one embodiment, the at least one cationic lipid comprises DOTMA and the at least one helper lipid comprises CHOL and POPC or the at least one helper lipid comprises CHOL, wherein the lipids of the lipid vesicular core of the particles of the present invention are composed of DOTMA/CHOL/POPC 10/50/40, DOTMA/CHOL/POPC 20/50/30, DOTMA/CHOL/POPC 30/50/20, DOTMA/CHOL/POPC 40/50/10, and DOTMA/CHOL/POPC 50/50/0 molar ratio, respectively.

The term "ethanol injection technique" refers to a process, in which an ethanol solution comprising lipids is rapidly dropped into an aqueous solution through a needle. This action disperses the lipids throughout the solution and promotes lipid vesicular core formation such as liposome formation.

The term "reverse phase evaporation technique" refers to a process, in which an organic solution comprising lipids is introduced into an aqueous solution such that a water/oil (w/o) emulsion is created. Thus, the organic solution and the aqueous solution should be immiscible. The organic solution is then removed from the water/oil emulsion, e.g. by evaporation. This process leads to lipid vesicular core formation such as liposome formation. The resulting solution can be further diluted with an aqueous solution in order to promote lipid vesicular core formation such as liposome formation.

Using the ethanol injection technique, the lipid vesicular core such as the positively charged lipid vesicular core having a therapeutic effective compound encapsulated therein is preferably formed as follows: an ethanol solution comprising lipids, such as cationic lipids like DMEPC, DOTMA and/or DOTAP, is injected into an aqueous solution comprising a therapeutically effective compound, e.g. a bisphosphonate, particularly aminobisphosphonate like zoledronic acid, e.g. under stirring.

Using the reverse phase evaporation technique, the lipid vesicular core such as the positively charged lipid vesicular core having a therapeutic effective compound encapsulated therein is preferably formed as follows: an aqueous solution comprising a therapeutically effective compound, e.g. a bisphosphonate, particularly aminobisphosphonate like zoledronic acid, is introduced into a mixture of lipids, such as cationic lipids like DMEPC, DOTMA and/or DOTAP, and an organic solvent. The above components are mixed or agitated, e.g. by sonication, so that a w/o emulsion is formed. Subsequently, the organic solvent is removed from the w/o emulsion, e.g. by evaporation. To support liposome formation, an aqueous solution may be added to the resulting solution for dilution.

The particles of the present invention are obtainable by adding RNA to the vesicular core such as the lipid vesicular core, e.g. the positively charged lipid vesicular core having the therapeutically effective compound encapsulated therein. In one embodiment, the particles of the present invention are obtainable by a process comprising a step of extruding and/or a step of lyophilizing the particle. Preferably, the particles are extruded, e.g. by filtration, trough a membrane having pores with a diameter of 0.02 to 1 µm, preferably of 0.3 to 0.6 µm or between 0.02 and 0.2 µm. It is to be understood, that the size of the pores are chosen in dependence of the desired size of the particles. It is preferred, that the membrane is a polycarbonate membrane or cellulose ester membrane. The not encapsulated therapeutically effective compound is preferably removed via dialysis.

The term "extruding" or "extrusion" refers to the creation of objects such as particles having a fixed, cross-sectional profile. In particular, it refers to the downsizing of a particle, preferably a liposome, whereby the particle is forced through filters with defined pores.

The term "lyophilizing" or "lyophilization" refers to the freeze-drying of a particle by freezing it and then reducing the surrounding pressure to allow the frozen medium in the particle to sublimate directly from the solid phase to the gas phase.

The term "therapeutically effective compound" relates to any compound being therapeutically effective when administered to an individual. The term "therapeutically effective compound" further relates to any agent that changes, preferably cures, alleviates or partially arrests the clinical manifestations of a given disease and its complications in a therapeutic intervention comprising the administration of said compound.

In one embodiment, the therapeutic effective compound encapsulated within the vesicular core of the particles of the present invention is water-soluble. Hydrophilic properties of the therapeutic effective compound may improve its encapsulating efficiency and prevent undesired release. It is preferred, that the therapeutic effective compound has a net negative charge. It is more preferred that the therapeutic effective compound is double negatively charged. In one embodiment, the therapeutically effective compound is a small molecule. A small size of the compound may further improve the encapsulating efficiency. Small molecule compounds are described to act as good antagonist, agonists or allosteric modulators of diverse targets.

In the present context, the term "treatment", "treating" or "therapeutic intervention" relates to the management and care of an individual for the purpose of combating a condition such as a disease or disorder. The term is intended to include the full spectrum of treatments for a given condition from which the individual is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications. The individual to be treated is an animal, preferably a mammal, in particular a human being. In the present context, the term "therapeutically effective amount" of a compound means an amount sufficient to cure, alleviate or partially arrest the clinical manifestations of a given disease and its complications in a therapeutic intervention comprising the administration of a compound. The desired reaction for a therapy of a disease or a condition may also be the retardation of the occurrence or the inhibition of the occurrence of the disease or the condition. An therapeutically effective amount of a compound according to the present invention is dependent on the condition or disease, the severity of the disease, the individual parameters of the individual, including age, physiological condition, height, and weight, the duration of the treatment, the type of an optionally accompanying therapy, the specific administration route, and similar factors.

Terms such as "RNA forming a hydrophilic shell" or "RNA decorating" according to the invention mean that at least one RNA molecule is positioned on the outside of a vesicular core. Preferably, the RNA does not substantially intercalate into the vesicular core. Preferably, a portion or the entire surface of the vesicular core is covered by the RNA. For example, at least 5%, at least 10%, at least 20%, at least 30%, at least 40%, at least 50%, at least 60%, at least 70%, at least 80%, at least 90%, or 100% of the surface of the vesicular core is covered by the RNA.

In the context of the present invention, the term "RNA" relates to a molecule which comprises ribonucleotide residues and preferably being entirely or substantially composed of ribonucleotide residues. The term "ribonucleotide" relates to a nucleotide with a hydroxyl group at the 2'-position of a β-D-ribofuranosylgroup. The term "RNA" comprises double-stranded RNA, single stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs, particularly analogs of naturally-occurring RNAs. The RNA used according to the present invention may have a known composition, or the composition of the RNA may be partially or entirely unknown. The term "mRNA" means "messenger-RNA" and relates to a transcript which is generated by using a DNA template and encodes a peptide or protein. Typically, mRNA comprises a 5'-UTR, a protein coding region, and a 3'-UTR. mRNA may be generated by in vitro transcription from a DNA template. The in vitro transcription methodology is known to the skilled person. For example, there is a variety of in vitro transcription kits commercially available. The term "antisense-RNA" relates to single-stranded RNA comprising ribonucleotide residues, which are complementary to the mRNA. The term "siRNA" means "small interfering RNA", which is a class of double-stranded RNA-molecules preferably comprising 20 to 25 base pairs. Preferably, siRNA is capable of binding specifically to a portion of the mRNA-molecule. This binding induces a process, in which the said portion of the mRNA-molecule is cut and thereby the gene expression of said mRNA-molecule inhibited. The term "microRNA" refers to a non-coding single-stranded RNA molecule preferably comprising 20 to 25 base pairs. Preferably, microRNA is capable of binding specifically to a portion of the mRNA-molecule. This binding induces a process, in which the translation of the said mRNA molecule and thereby the gene expression of said mRNA molecule is inhibited. The RNA may be modified by a 5'-cap or 5'-cap analog, e.g. achieved by in vitro transcription of a DNA template in presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus. The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

The cDNA containing vector template may comprise vectors carrying different cDNA inserts which following transcription results in a population of different RNA molecules optionally capable of expressing different peptides or proteins or may comprise vectors carrying only one species of cDNA insert which following transcription only results in a population of one RNA species capable of expressing only one peptide or protein. Thus, it is possible to produce RNA capable of expressing a single peptide or protein only or to produce compositions of different RNAs capable of expressing more than one peptide or protein, e.g. a composition of peptides or proteins.

The term "expression" is used herein in its broadest meaning and comprises the production of RNA or of RNA and protein. With respect to RNA, the term "expression" or "translation" relates in particular to the production of peptides or proteins. Expression may be transient or may be stable.

According to the present invention, the RNA can be coding RNA, i.e. RNA encoding a peptide or protein. Said RNA may express the encoded peptide or protein. For example, said RNA may be RNA encoding and expressing an antigen or an immunologically active compound (which does not encode an antigen). Alternatively, the RNA can be non-coding RNA such as antisense-RNA, micro RNA (miRNA) or siRNA.

According to the invention, RNA forming a hydrophilic shell on at least a portion of a vesicular core preferably comprises or consists of pharmaceutically active RNA.

A "pharmaceutically active RNA" is a RNA that encodes a pharmaceutically active peptide or protein or is pharmaceutically active in its own, e.g., it has one or more pharmaceutical activities such as those described for pharmaceutically active proteins. For example, the RNA may be one or more strands of RNA interference (RNAi). Such agents include short interfering RNAs (siRNAs), or short hairpin RNAs (shRNAs), or precursor of a siRNA or microRNA-like RNA, targeted to a target transcript, e.g., a transcript of an endogenous disease-related transcript of a subject.

A "pharmaceutically active peptide or protein" has a positive or advantageous effect on the condition or disease state of a subject when administered to the subject in a therapeutically effective amount. Preferably, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" includes peptides and proteins that are antigens, i.e., administration of the peptide or protein to a subject elicits an immune response in a subject which may be therapeutic or partially or fully protective.

Examples of pharmaceutically active proteins include, but are not limited to, cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthestic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

In one particularly preferred embodiment of the invention, the RNA forming a hydrophilic shell on at least a portion of a vesicular core comprises RNA that encodes a cytokine which is involved in and preferably induces or enhances development, priming, expansion, differentiation and/or survival of T cells, preferably an interleukin such as an interleukin selected from the group consisting of IL-2, IL-7, IL-12, IL-15, and IL-21, and the at least one therapeutically effective compound encapsulated within the vesicular core comprises an agent stimulating γδ T cells such as zoledronic acid.

According to the present invention, the term "peptide" comprises oligo- and polypeptides and refers to substances comprising two or more, preferably three or more, preferably four or more, preferably six or more, preferably eight or more, preferably ten or more, preferably 14 or more, preferably 16 or more, preferably 21 or more and up to preferably 8, 10, 20, 30, 40, or 50, in particular 100 amino acids joint covalently by peptide bonds. The term "protein" refers to large peptides, preferably to peptides with more than 100 amino acid residues, but in general the terms "peptides" and "proteins" are synonymous and are used interchangeably herein.

According to the invention, the term "RNA encoding" means that the RNA, if present in the appropriate environment, preferably within a cell, can direct the assembly of amino acids to produce the protein or peptide is encodes during the process of translation. Preferably, RNA according to the invention is able to interact with the cellular translation machinery allowing translation of the protein or peptide.

According to the present invention, the RNA is preferably negatively charged and is capable of forming complexes with cationic lipids and, in particular, covering the surface or portions of a positively charged lipid vesicular core such as a liposome comprising cationic lipids.

The term "net charge of the particle" relates to the total sum of charges, such as positive and negative charges. For example, if the particle comprises a higher number of negative charges than positive charges, the net charge of the particle is negative. If the particle comprises a higher number of positive charges than negative charges, the net charge of the particle is positive. If the particle comprises an equal number of positive charges and negative charges, the net charge of the particle is neutral, particularly electroneutral. Thus, the net charge of the particle according to the present invention can be negative, positive or neutral. Preferably, the net charge of the particle is negative.

The term "average diameter" refers to the mean diameter of the particles and may be calculated by dividing the sum of the diameter of each particle by the total number of particles. Although the term "diameter" is used normally to refer to the maximal length of a line segment passing through the centre and connecting two points on the periphery of a spherical object, it is also used herein to refer to the maximal length of a line segment passing through the center and connecting two points on the periphery of particles having a substantial spherical shape or other shapes.

The term "antigen" relates to an agent comprising an epitope against which an immune response is to be generated. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen is preferably presentable by cells of the immune system such as antigen presenting cells like dendritic cells or macrophages. In addition, an antigen or a processing product thereof is preferably recognizable by a T or B cell receptor, or by an immunoglobulin molecule such as an antibody. In a preferred embodiment, the antigen is a disease-associated antigen, such as a tumor antigen, a viral antigen, or a bacterial antigen.

The term "tumor antigen" refers to a constituent of cancer cells which may be derived from the cytoplasm, the cell surface and the cell nucleus. In particular, it refers to those antigens which are produced, preferably in large quantity, intracellularly or as surface antigens on tumor cells. Examples for tumor antigens include HER2, EGFR, VEGF, CAMPATH1-antigen, CD22, CA-125, HLA-DR, Hodgkin-lymphoma or mucin-1, but are not limited thereto.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "disease-associated antigen" is used in it broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may therefore be used for therapeutic purposes. Disease-associated antigens are preferably associated with infection by microbes, typically microbial antigens, or associated with cancer, typically tumors.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

The term "disease involving an antigen" refers to any disease which implicates an antigen, e.g. a disease which is characterized by the presence of an antigen. The disease involving an antigen can be an infectious disease, an autoimmune disease, or a cancer disease or simply cancer. As mentioned above, the antigen may be a disease-associated antigen, such as a tumor-associated antigen, a viral antigen, or a bacterial antigen.

The term "infectious disease" refers to any disease which can be transmitted from individual to individual or from organism to organism, and is caused by a microbial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

The term "autoimmune disease" refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

The term "immune response" relates to a reaction of the immune system such as to immunogenic organisms, such as bacteria or viruses, cells or substances. The term "immune response" includes the innate immune response and the adaptive immune response. Preferably, the immune response is related to an activation of immune cells, an induction of cytokine biosynthesis and/or antibody production.

It is preferred that the immune response induced by the particles of the present invention comprises the steps of activation of antigen presenting cells, such as dendritic cells and/or macrophages, presentation of an antigen or fragment thereof by said antigen presenting cells and activation of cytotoxic T cells due to this presentation.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also downregulate other aspects of the immune response, for example shifting the immune response away from a TH2 immune response, which is useful for treating a wide range of TH2 mediated diseases. Immunologically active compounds can be useful as vaccine adjuvants. In one embodiment, the RNA forming a hydrophilic shell on at least a portion of the vesicular core of the particles of the present invention encodes an immunologically active compound. Said compound preferably does not encode an antigen.

The term "immune cells" refers to cells of the immune system involved in defending the body of an individual. The term "immune cells" encompasses specific types of immune cells and their precursors including leucocytes comprising macrophages, monocytes (precursors of macrophages), granulocytes such as neutrophils, eosinophils and basophils, dendritic cells, mast cells, and lymphocytes such as B cells, T cells and natural killer (NK) cells. Macrophages, monocytes (precursors of macrophages), neutrophils, dendritic cells, and mast cells are phagocytic cells.

The term "phagocytic cells" refers to cells that protect the body of an individual by ingesting (phagocytosing) harmful foreign particles, bacteria, and dead or dying cells.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells. Preferably, the macrophages are splenic macrophages.

The term "dendritic cell" (DC) refers to another subtype of phagocytic cells belonging to the class of antigen presenting cells. Preferably, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. Preferably, the dendritic cells are splenic dendritic cells.

The term "antigen presenting cell" (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

The term "maturation" is defined herein as the action of immature highly phagocytic dendritic cells and macrophages resulting in phenotypic and/or functional modifications of these cells. Especially, in dendritic cells, the associated phenotypic modification is represented by an increase of CD40, CD80, CD86, CD83, MHC class I and II molecule cell surface expression and/or a decrease of CD 14 molecule cell surface expression. The functional changes may be the loss of phagocytic properties, the acquisition of migration abilities, an increased allogeneic T cell stimulation efficiency and changes in the cytokine and chemokine expression profile, and particularly an increased IL-12 secretion. The IL-12 production by DCs is critical for their in vivo function, since this cytokine has been shown to generate a polarization of the immune response towards the Th1 pathway in vivo. A Th1 type immune response is considered as immune response involving stimulation of antigen specific T lymphocytes CD8+, whereas a Th2 type immune response involves rather a stimulation of antibody response and eventually unresponsiveness of the cytotoxic lymphocytes to an antigen.

If, according to the present invention, it is desired to induce or enhance an immune response by using particles as described herein, the immune response may be triggered or enhanced by the therapeutically effective compound encapsulated within the vesicular core. For example, the therapeutically effective compound may stimulate certain immune cells such as T cells. Preferably, said T cells are γδ T cells, more preferably Vγ9Vδ2 T cells. Alternatively or additionally, the immune response may be triggered or enhanced by the RNA forming a hydrophilic shell on at least a portion of the vesicular core of the particles. For example, proteins or peptides encoded by the RNAs or procession products thereof may be presented by major histocompatibility complex (MHC) proteins expressed on antigen presenting cells. The MHC peptide complex can then be recognized by immune cells such as T cells or B cells leading to their activation.

The terms "T-cells" or "T lymphocytes" relate to types of lymphocytes that play a central role in cell-mediated immunity. T-cells or T lymphocytes can be distinguished from other lymphocytes, such as B cells and natural killer (NK) cells, by the presence of a T cell receptor (TCR) on the cell surface. They do not have antigen presenting properties (but rather, requiring B cells or NK cells for its antigen-presenting property). They are called T cells because they mature in the thymus. T cells are capable of recognizing an antigen when displayed on the surface of antigen presenting cells or matrix together with one or more MHC molecules or one or more non-classical MHC molecules.

The term "γδ T cells" (gamma delta T cells) relates to a subset of T cells that possess a distinct T cell receptor (TCR) on their surface. A majority of T cells have a TCR composed of two glycoprotein chains called α- and β-TCR chains. In contrast, in γδ T cells, the TCR is made up of one γ-chain and one δ-chain. This group of T cells is usually much less common than αβ T cells. Human γδ T cells play an important role in stress-surveillance responses like infectious diseases and autoimmunity. Transformation-induced changes in tumors are also suggested to cause stress-surveillance responses mediated by γδ T cells and enhance antitumor immunity. Importantly, after antigen engagement, activated γδ T cells at lesional sites provide cytokines (e.g. INFγ, TNFα) and/or chemokines mediating recruitment of other effector cells and show immediate effector functions such as cytotoxicity (via death receptor and cytolytic granules pathways) and ADCC.

The majority of γδ T cells in peripheral blood express the Vγ9Vδ2 T cell receptor (TCRγδ). The term "Vγ9Nδ2 T cells" relates to cells which constitute the major γδ T cell population in human peripheral blood. Vγ9Vδ2 T cells are unique to humans and primates and are assumed to play an early and essential role in sensing "danger" by invading pathogens as they expand dramatically in many acute infections and may exceed all other lymphocytes within a few days, e.g. in tuberculosis, salmonellosis, ehrlichiosis, brucellosis, tularemia, listeriosis, toxoplasmosis, and malaria.

γδ T cells respond to small non-peptidic phosphorylated antigens (phosphoantigens) such as pyrophosphates synthesized in bacteria and isopentenyl pyrophosphate (IPP) produced in mammalian cells through the mevalonate pathway. Whereas IPP production in normal cells is not sufficient for activation of γδ T cells, dysregulation of the mevalonate pathway in tumor cells leads to accumulation of IPP and γδ T cell activation. IPPs can also be therapeutically increased by aminobisphosphonates, which inhibit the mevalonate pathway enzyme farnesyl pyrophosphate synthase (FPPS). Among others, zoledronic acid (ZA, zoledronate, Zometa™, Novartis) represents such an aminobiphosphonate, which is already clinically administered to patients for the treatment of osteoporosis and metastasic bone disease. Upon treatment of PBMCs in vitro, ZA is taken up especially by monocytes. IPP accumulates in the monocytes and they differentiate to antigen-presenting cells stimulating development of γδ T cells. In this setting, the addition of interleukin-2 (IL-2) is preferred as growth and survival factor for activated γδ T cells. Finally, certain alkylated amines have been described to activate Vγ9Vδ2 T cells in vitro, however only at millimolar concentrations.

According to the invention, the term "agent stimulating γδ T cells" relates to compounds stimulating development of γδ T cells, in particular Vγ9Vδ2 T cells, in vitro and/or in vivo, in particular by inducing activation and expansion of γδ T cells. Preferably, the term relates to compounds which in vitro and/or in vivo increase isopentenyl pyrophosphate (IPP) produced in mammalian cells, preferably by inhibiting the mevalonate pathway enzyme farnesyl pyrophosphate synthase (FPPS).

One particular group of compounds stimulating γδ T cells are bisphosphonates, in particular nitrogen-containing bisphosphonates (N-bisphosphonates; aminobisphosphonates). According to the invention, zoledronic acid (INN) or zoledronate (marketed by Novartis under the trade names Zometa, Zomera, Aclasta and Reclast) is a particularly preferred bisphosphonate. Zometa is used to prevent skeletal fractures in patients with cancers such as multiple myeloma and prostate cancer, as well as for treating osteoporosis. It can also be used to treat hypercalcemia of malignancy and can be helpful for treating pain from bone metastases.

The terms "stimulating T cells" or "stimulation of T cells" refer to the induction or activation of a T cell response by a primary signal, such as by the interaction with an antigen-MHC class II complex through the T cell antigen receptor. The term also includes the co-stimulation of T cells, such as through cytokines (e.g. CD80 or CD86 proteins). A T cell is activated if it has received a primary signaling event which initiates an immune response by the T cell.

The term "priming T cells" refers to the induction of a first contact of the T cell with its specific antigen (e.g. by dendritic cells presenting the antigen to T cells), which causes the differentiation of the T cell into an effector T cell (e.g. a cytotoxic T cell or a T helper cell).

The terms "expanding T cells" or "expansion of T cells" refer to the increase of the number of T cells, preferably T cells specifically recognizing an antigen. It is preferred, that the number of T cells specifically recognizing an antigen, e.g. an antigen encoded from the RNA decorating the particle of the present invention, or a procession product of the antigen increases. The antigen or procession product of the antigen is preferably presented in the context of MHC molecules, such as on the surface of antigen presenting cells like dendritic cells or macrophages.

The term "immunotherapy" relates to the treatment of a disease or condition by inducing, enhancing, or suppressing an immune response. Immunotherapies designed to elicit or amplify an immune response are classified as activation immunotherapies, while immunotherapies that reduce or suppress an immune response are classified as suppression immunotherapies. The term "immunotherapy" includes antigen immunization or antigen vaccination, or tumor immunization or tumor vaccination. The term "immunotherapy" also relates to the manipulation of immune responses such that inappropriate immune responses are modulated into more appropriate ones in the context of autoimmune diseases such as rheumatic arthritis, allergies, diabetes or multiple sclerosis.

The terms "immunization" or "vaccination" describe the process of administering an antigen to an individual with the purpose of inducing an immune response, for example, for therapeutic or prophylactic reasons.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "protect", "prevent", "prophylactic", "preventive", or "protective" relate to the prevention and/or treatment of the occurrence and/or the propagation of a disease, e.g. tumor, in an individual. For example, a prophylactic administration of an immunotherapy, e.g. by administering the pharmaceutical composition of the present invention, can protect the receiving individual from the development of a tumor. For example, a therapeutic administration of an immunotherapy, e.g. by administering the pharmaceutical composition of the present invention, can stop the development of a disease, e.g. lead to the inhibition of the progress/growth of a tumor. This comprises the deceleration of the progress/growth of the tumor, in particular a disruption of the progression of the tumor, which preferably leads to elimination of the tumor. A therapeutic administration of an immunotherapy may protect the individual, for example, from the dissemination or metastasis of existing tumors.

The term "water-soluble compound" refers to any ionic compound (or salt) which is able to dissolve in water. Generally, the underlying solvation arises because of the attraction between positive and negative charges of the compound with the partially negative and partially positive charges of the $H_2O$-molecules, respectively. Compounds which dissolve in water are also termed "hydrophilic" ("water-loving"). Water solubility ($S_W$), also known as aqueous solubility, is the maximum amount of a substance that can dissolve in water at equilibrium at a given temperature and pressure. Generally, the limited amount is given by the solubility product. Following the definition of solubility in the European. Pharmacopoeia, "sparingly soluble" means that the approximate volume of solvent in milliliters per gram of solute is from 30 to 100 (at a temperature between 15° C. and 25° C.), "soluble" means that the approximate volume of solvent in milliliters per gram of solute is from 10 to 30 (at a temperature between 15° C. and 25° C.), "freely soluble" means that the approximate volume of solvent in milliliters per gram of solute is from 1 to 10 (at a temperature between 15° C. and 25° C.), and "very soluble" means that the approximate volume of solvent in milliliters per gram of solute is less than 1 (at a temperature between 15° C. and 25° C.). For purposes of the present invention, RNA is considered a hydrophilic compound and a shell formed by RNA is considered a "hydrophilic shell".

The term "small molecule compound" refers to a molecule that can act to affect biological processes. Small molecules can include any number of therapeutic agents presently known and used, or can be small molecules synthesized in a library of such molecules for the purpose of screening for biological function(s). The small molecule compound usually have a molecular weight less than about 5,000 daltons (Da), preferably less than about 2,500 Da, more preferably less than 1,000 Da, most preferably less than about 500 Da. The small molecule compound preferably serves as regulating molecule of biological processes such as an enzyme substrate, an antagonist, or an allosterically activating or an allosterically inhibiting molecule. It is preferred, that the molecule is capable of binding to another molecule, such as a protein, nucleic acid or polysaccharide, and acting as an effector, altering the activity of the other molecule.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient".

The term "patient" means an individual or subject for treatment, in particular a diseased individual or subject, including human beings, non-human primates or another animals, in particular mammals such as cows, horses, pigs, sheeps, goats, dogs, cats or rodents such as mice and rats. In particularly preferred embodiments of the present invention, the patient is a human being.

The particles of the present invention may be administered in the form of any suitable pharmaceutical composition. The term "pharmaceutical composition" relates to a formulation comprising a therapeutically effective agent or a salt thereof, preferably together with pharmaceutical excipients such as buffers, preservatives and tonicity modifiers. Said pharmaceutical composition is useful for treating, preventing, or reducing the severity of a disease or disorder by administration of said pharmaceutical composition to an individual. A pharmaceutical composition is also known in the art as a pharmaceutical formulation. The pharmaceutical composition can be administered locally or systemically, preferably systemically. In the context of the present invention, the pharmaceutical composition comprises the particle of the invention. This particle is therapeutically effective.

The term "systemic administration" refers to the administration of a therapeutically effective agent such that the agent becomes widely distributed in the body of an individual in significant amounts and develops a biological effect. For example, the agent may develop its desired effect in the blood and/or reaches its desired site of action via the vascular system. Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of a therapeutically effective agent such that the agent does not pass the intestine. The term "parenteral administration" includes intravenous administration, subcutaneous administration, intradermal administration or intraarterial administration but is not limited thereto.

The pharmaceutical compositions of the present invention preferably comprise at least one adjuvant. The term "adjuvant" relates to compounds, which when administered in combination with an antigen or antigen peptide to an individual, prolongs or enhances or accelerates an immune response. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B cells, macrophages, dendritic cells, T cells and unspecific activation of immune cells. Adjuvants comprise a heterogeneous group of compounds such as oil emulsions (e.g., Freund's adjuvants), mineral compounds (such as alum), bacterial products (such as Bordetella pertussis toxin), or immune-stimulating complexes. Examples for adjuvants include saponins, incomplete Freund's adjuvants, complete Freund's adjuvants, tocopherol or alum, but are not limited thereto.

The pharmaceutical composition according to the present invention is generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the particles or compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the particles or compositions described herein may depend on various of such parameters. In the case that a reaction in a patient is insufficient with an initial dose, higher doses (or effectively higher doses achieved by a different, more localized route of administration) may be used.

The pharmaceutical compositions of the present invention may contain salts, buffers, preserving agents, carriers and optionally other therapeutic agents. Preferably, the pharmaceutical compositions of the present invention comprise one or more pharmaceutically acceptable carriers, diluents and/or excipients.

The term "excipient" is intended to indicate all substances in a pharmaceutical composition which are not active ingredients such as binders, lubricants, thickeners, surface active agents, preservatives, emulsifiers, buffers, flavoring agents, or colorants.

The term "diluent" relates a diluting and/or thinning agent. Moreover, the term "diluent" includes any one or more of fluid, liquid or solid suspension and/or mixing media.

The term "carrier" relates to one or more compatible solid or liquid fillers or diluents, which are suitable for an administration to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol and water.

Pharmaceutical carriers, excipients or diluents can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

The terms "reducing" or "inhibiting" or similar phrases relate to the ability to cause an overall decrease, preferably of at least 5%, at least 10%, at least 20%, at least 30%, at least 40%, at least 50%, at least 80%, or at least 100% in the level, e.g. expression level, particularly compared to a control. The terms "reduce" or "inhibit" or similar phrases include a complete or essentially complete reduction or inhibition, i.e. a reduction or inhibition to zero or essentially zero, particularly compared to a control.

The terms "increasing" or "enhancing" or similar phrases relate to the ability to cause an overall increase or enhancement, preferably of at least 5%, at least 10%, at least 20%, at least 30%, at least 40%, at least 50%, at least 80%, or at least 100% in the level, e.g. expression level, particularly compared to a control.

The term "RNA accumulation" refers to the enrichment of RNA in its broadest sense. Preferably, the enrichment is a local enrichment in a body, organ, tissue, cell type, cell organelles or cell compartment. The term "RNA accumulation" preferably relates to a concentration increase of at least 10%, at least 20%, at least 30%, at least 40%, at least 50%, at least 80%, or at least 100%. According to the present invention, the term "RNA accumulation" can mean a concentration increase of the RNA over time in an individual, organ, tissue, cell type, cell organelle or cell compartment (e.g. change of RNA concentration before and after treatment) or can refer to concentration differences between different individuals, organs, tissues, cell-types, cell organelles or cell compartments (e.g. RNA concentration difference between lung and spleen).

It is preferred in one embodiment that the RNA decorating the particles of the present invention, after systemic administration, accumulates and/or is expressed in the spleen. It is further preferred that no or essentially no RNA accumulation and/or RNA expression is induced by the systemic administration of the particles of the present invention in the lung and/or liver. Preferably, RNA accumulation and/or RNA expression in the spleen is at least 5-fold, at least 10-fold, at least 20-fold, at least 30-fold, at least 40-fold, at least 50-fold the amount of RNA accumulation and/or RNA expression in the lung.

In one embodiment, the particles of the present invention are targeted to the spleen for activating splenic antigen presenting cells. Thus, it is preferred that after systemic administration of the particles of the present invention RNA accumulation and/or RNA expression in antigen presenting cells occurs. Antigen presenting cells are preferably professional antigen presenting cells or non-professional antigen presenting cells. More preferably, the professional antigen presenting cells are dendritic cells and/or macrophages, even more preferably splenic dendritic cells and/or splenic macrophages.

In one preferred embodiment, the systemic administration of the particles of the present invention results in an increase of the expression of at least one maturation marker in dendritic cells and/or macrophages such as splenic dendritic cells and/or splenic macrophages. Preferably, the maturation marker is selected from the group consisting of CD40, CD80, CD86, CD83, MHC class I and II molecules such as HLA-DR. More preferably, the maturation marker is selected from the group consisting of CD40, CD86, and MHC class II molecules. Even more preferably, the maturation marker is selected from the group consisting of CD40, CD86, and HLA-DR.

The term "about" means greater or less than the value or range of values stated by 1/10 of the stated values, but is not intended to limit any value or range of values. For instance, a concentration value of about 30% means a concentration between 27% and 33%. Each value or range of values preceded by the term "about" is also intended to encompass the embodiment of the stated absolute value or range of values.

As mentioned above, RNA according to the present invention covers at least a portion of the vesicular core. The term "portion" refers to a fraction. With respect to a particular structure such as the surface of a vesicular core, the term "portion thereof" may designate a continuous or a discontinuous fraction thereof. A portion of the surface of the vesicular core may comprise at least 1%, at least 5%, at least 10%, at least 20%, at least 30%, preferably at least 40%, preferably at least 50%, preferably at least 60%, more preferably at least 70%, even more preferably at least 80%, even more preferably at least 90%, and most preferably 100% of the surface of the vesicular core. The surface coverage with RNA can easily be controlled. It depends, for example, on the amount of RNA and the amount of positively charged lipids used for the formation of the particles of the present invention. Thereby, the surface properties of the particles of the present invention can be influenced and, thus, the immune inducing potential or the immune modulating potential of said particle can be varied.

The agents and compositions provided herein may be used alone or in combination with conventional therapeutic regimens such as surgery, irradiation, chemotherapy and/or bone marrow transplantation (autologous, syngeneic, allogeneic or unrelated).

In particular, treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment of the present invention, a cancer treatment using the particles of the invention may be effectively combined with various other drugs. Among those are e.g. combinations with conventional tumor therapies, multi-epitope strategies, additional immunotherapy, and treatment approaches targeting angiogenesis or apoptosis (for review see e.g. Andersen et al. 2008: Cancer treatment: the combination of vaccination with other therapies. Cancer Immunology Immunotherapy, 57(11): 1735-1743.) Sequential administration of different agents may inhibit cancer cell growth at different check points, while other agents may e.g. inhibit neo-angiogenesis, survival of malignant cells or metastases, potentially converting cancer into a chronic disease. The following list provides some non-limiting examples of anti-cancer drugs and therapies which can be used in combination with the present invention:

1. Chemotherapy

Chemotherapy is the standard of care for multiple types of cancer. The most common chemotherapy agents act by killing cells that divide rapidly, one of the main properties of cancer cells. Thus, a combination with conventional chemotherapeutic drugs such as e.g. alkylating agents, antimetabolites, anthracyclines, plant alkaloids, topoisomerase inhibitors, and other antitumour agents which either affect cell division or DNA synthesis may significantly improve the therapeutic effects of the present invention by clearing suppressor cells, reboot of the immune system, by rendering tumor cells more susceptible to immune mediated killing, or by additional activation of cells of the immune system. A synergistic anti-cancer action of chemotherapeutic and vaccination-based immunotherapeutic drugs has been demonstrated in multiple studies (see e.g. Quoix et al. 2011: Therapeutic vaccination with TG4010 and first-line chemotherapy in advanced non-small-cell lung cancer: a controlled phase 2B trial. Lancet Oncol. 12(12): 1125-33.; see also Liseth et al. 2010: Combination of intensive chemotherapy and anticancer vaccines in the treatment of human malignancies: the hematological experience. J Biomed Biotechnol. 2010: 6920979; see also Hirooka et al 2009: A combination therapy of gemcitabine with immunotherapy for patients with inoperable locally advanced pancreatic cancer. Pancreas 38(3): e69-74). There are hundreds of chemotherapeutic drugs available which are basically suitable for combination therapies. Some (non-limiting) examples of chemotherapeutic drugs which can be combined with the present invention are carboplatin (Paraplatin), cisplatin (Platinol, Platinol-AQ), cyclophosphamide (Cytoxan, Neosar), docetaxel (Taxotere), doxorubicin (Adriamycin), erlotinib (Tarceva), etoposide (VePesid), fluorouracil (5-FU), gemcitabine (Gemzar), imatinib mesylate (Gleevec), irinotecan (Camptosar), methotrexate (Folex, Mexate, Amethopterin), paclitaxel (Taxol, Abraxane), sorafinib (Nexavar), sunitinib (Sutent), topotecan (Hycamtin), vincristine (Oncovin, Vincasar PFS), and vinblastine (Velban).

2. Surgery

Cancer surgery—an operation to remove the tumor—remains the foundation of cancer treatment. Surgery can be combined with other cancer treatments in order to delete any remaining tumor cells. Combining surgical methods with subsequent immunotherapeutic treatment is a promising approach which has been demonstrated countless times.

3. Radiation

Radiation therapy remains an important component of cancer treatment with approximately 50% of all cancer patients receiving radiation therapy during their course of illness. The main goal of radiation therapy is to deprive cancer cells of their multiplication (cell division) potential. The types of radiation used to treat cancer are photons radiation (x-rays and gamma rays) and particle radiations (electron, proton and neutron beams.) There are two ways to deliver the radiation to the location of the cancer. External beam radiation is delivered from outside the body by aiming high-energy rays (photons, protons or particle radiation) to the location of the tumor. Internal radiation or brachytherapy is delivered from inside the body by radioactive sources, sealed in catheters or seeds directly into the tumor site. Radiation therapy techniques which are applicable in combination with the present invention are e.g. fractionation (radiation therapy delivered in a fractionated regime, e.g. daily fractions of 1.5 to 3 Gy given over several weeks), 3D conformal radiotherapy (3DCRT; delivering radiation to the gross tumor volume), intensity modulated radiation therapy (IMRT; computer-controlled intensity modulation of multiple radiation beams), image guided radiotherapy (IGRT; a technique comprising pre-radiotherapy imaging which allows for correction), and stereotactic body radiation therapy (SRBT, delivers very high individual doses of radiation over only a few treatment fractions). For a radiation therapy review see Baskar et al. 2012: Cancer and radiation therapy: current advances and future directions. Int. J Med Sci. 9(3): 193-199.

4. Antibodies

Antibodies (preferably monoclonal antibodies) achieve their therapeutic effect against cancer cells through various mechanisms. They can have direct effects in producing apoptosis or programmed cell death. They can block components of signal transduction pathways such as e.g. growth factor receptors, effectively arresting proliferation of tumor cells. In cells that express monoclonal antibodies, they can bring about anti-idiotype antibody formation. Indirect effects include recruiting cells that have cytotoxicity, such as monocytes and macrophages. This type of antibody-mediated cell kill is called antibody-dependent cell mediated cytotoxicity (ADCC). Antibodies also bind complement, leading to direct cell toxicity, known as complement dependent cytotoxicity (CDC). Combining surgical methods with immunotherapeutic drugs or methods is an successful approach, as e.g. demonstrated in Gadri et al. 2009: Synergistic effect of dendritic cell vaccination and anti-CD20 antibody treatment in the therapy of murine lymphoma. J Immunother. 32(4): 333-40. The following list provides some non-limiting examples of anti-cancer antibodies and potential antibody targets (in brackets) which can be used in combination with the present invention: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Bavituximab (phosphatidylserine), Bectumomab (CD22), Belimumab (BAFF), Bevacizumab (VEGF-A), Bivatuzumab mertansine (CD44 v6), Blinatumomab (CD19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin $\alpha v \beta 3$), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-$\beta$), Galiximab (CD80), Ganitumab (IGF-I), Gemtuzumab ozogamicin (CD33), Gevokizumab (IL-1$\beta$), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Narnatumab (RON), Necitumumab (EGFR), Nimotuzumab (EGFR), Nivolumab (IgG4), Ofatumumab (CD20), Olaratumab (PDGF-R $\alpha$), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzumab (HER2/neu), Pintumomab (adenocarcinoma antigen), Pritumumab (vimentin), Racotumomab (N-glycolyl-neuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL-6), Tabalumab (BAFF), Tacatuzumab tetraxetan (alpha-fetoprotein), Taplitumomab paptox (CD19), Tenatumomab (tenascin C), Teprotumumab (CD221), Ticilimumab (CTLA-4), Tigatuzumab (TRAIL-R2), TNX-650 (IL-13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1BB), Volociximab (integrin $\alpha 5 \beta 1$), Votumumab (tumor antigen CTAA16.88), Zalutumumab (EGFR), Zanolimumab (CD4).

5. Cytokines, Chemokines, Costimulatory Molecules, Fusion Proteins

Combined usage of the pharmaceutical compositions of the present invention such as the antigen-coding pharmaceutical compositions of the present invention with cytokines, chemokines, costimulatory molecules and/or fusion proteins thereof to evoke beneficial immune modulation or tumor inhibition effects is another embodiment of the present invention. In order to increase the infiltration of immune cells into the tumor and facilitate the movement of antigen-presenting cells to tumor-draining lymph nodes, various chemokines with C, CC, CXC and CX3C structures might be used. Some of the most promising chemokines are e.g CCR7 and its ligands CCL19 and CCL21, furthermore CCL2, CCL3, CCL5, and CCL16. Other examples are CXCR4, CXCR7 and CXCL12. Furthermore, costimulatory or regulatory molecules such as e.g. B7 ligands (B7.1 and B7.2) are useful. Also useful are other cytokines such as e.g. interleukins especially (e.g. IL-1 to IL17), interferons (e.g. IFNalpha1 to IFNalpha8, IFNalpha10, IFNalpha13, IFNalpha14, IFNalpha16, IFNalpha17, IFNalpha21, IFNbeta1, IFNW, IFNE1 and IFNK), hematopoietic factors, TGFs (e.g. TGF-$\alpha$, TGF-$\beta$, and other members of the TGF family), finally members of the tumor necrosis factor family of receptors and their ligands as well as other stimulatory molecules, comprising but not limited to 4-1BB, 4-1BB-L, CD137, CD137L, CTLA-4GITR, GITRL, Fas, Fas-L, TNFR1, TRAIL-R1, TRAIL-R2, p75NGF-R, DR6, LT.beta.R, RANK, EDAR1, XEDAR, Fn114, Troy/Trade, TAJ, TNFRII, HVEM, CD27, CD30, CD40, 4-1BB, OX40, GITR, GITRL, TACI, BAFF-R, BCMA, RELT, and CD95 (Fas/APO-1), glucocorticoid-induced TNFR-related protein, TNF receptor-related apoptosis-mediating protein (TRAMP) and death receptor-6 (DR6). Especially CD40/CD40L and OX40/OX40L are important targets for combined immunotherapy because of their direct impact on T cell survival and proliferation. For a review see Lechner et al. 2011: Chemokines, costimulatory molecules and fusion proteins for the immunotherapy of solid tumors. Immunotherapy 3 (11), 1317-1340.

6. Bacterial Treatments

Researchers have been using anaerobic bacteria, such as *Clostridium novyi*, to consume the interior of oxygen-poor tumours. These should then die when they come in contact with the tumour's oxygenated sides, meaning they would be harmless to the rest of the body. Another strategy is to use anaerobic bacteria that have been transformed with an enzyme that can convert a non-toxic prodrug into a toxic drug. With the proliferation of the bacteria in the necrotic and hypoxic areas of the tumour, the enzyme is expressed solely in the tumour. Thus, a systemically applied prodrug is metabolised to the toxic drug only in the tumour. This has been demonstrated to be effective with the nonpathogenic anaerobe *Clostridium sporogenes*.

7. Kinase Inhibitors

Another large group of potential targets for complementary cancer therapy comprises kinase inhibitors, because the growth and survival of cancer cells is closely interlocked with the deregulation of kinase activity. To restore normal kinase activity and therefor reduce tumor growth a broad range of inhibitors is in used. The group of targeted kinases comprises receptor tyrosine kinases e.g. BCR-ABL, B-Raf, EGFR, HER-2/ErbB2, IGF-IR, PDGFR-$\alpha$, PDGFR-$\beta$, c-Kit, Flt-4, Flt3, FGFR1, FGFR3, FGFR4, CSF1R, c-Met, RON, c-Ret, ALK, cytoplasmic tyrosine kinases e.g. c-SRC, c-YES, Abl, JAK-2, serine/threonine kinases e.g. ATM, Aurora A & B, CDKs, mTOR, PKCi, PLKs, b-Raf, S6K, STK11/LKB1 and lipid kinases e.g. PI3K, SKI. Small molecule kinase inhibitors are e.g. PHA-739358, Nilotinib, Dasatinib, and PD166326, NSC 743411, Lapatinib (GW-572016), Canertinib (CI-1033), Semaxinib (SU5416), Vatalanib (PTK787/ZK222584), Sutent (SU11248), Sorafenib (BAY 43-9006) and Leflunomide (SU101). For more information see e.g. Zhang et al. 2009: Targeting cancer with small molecule kinase inhibitors. Nature Reviews Cancer 9, 28-39.

8. Toll-Like Receptors

The members of the Toll-like receptor (TLRs) family are an important link between innate and adaptive immunity and the effect of many adjuvants rely on the activation of TLRs.

A large number of established vaccines against cancer incorporate ligands for TLRs for boosting vaccine responses. Besides TLR2, TLR3, TLR4 especially TLR7 and TLR 8 have been examined for cancer therapy in passive immunotherapy approaches. The closely related TLR7 and TLR8 contribute to antitumor responses by affecting immune cells, tumor cells, and the tumor microenvironment and may be activated by nucleoside analogue structures. All TLR's have been used as stand-alone immunotherapeutics or cancer vaccine adjuvants and may be synergistically combined with the formulations and methods of the present invention. For more information see van Duin et al. 2005: Triggering TLR signaling in vaccination. Trends in Immunology, 27(1):49-55.

9. Angiogenesis Inhibitors

In addition to therapies which target immune modulatory receptors affected by tumor-mediated escape mechanisms and immune suppression there are therapies which target the tumor environment. Angiogenesis inhibitors prevent the extensive growth of blood vessels (angiogenesis) that tumors require to survive. The angiogenesis promoted by tumor cells to meet their increasing nutrient and oxygen demands for example can be blocked by targeting different molecules. Non-limiting examples of angiogenesis-mediating molecules or angiogenesis inhibitors which may be combined with the present invention are soluble VEGF (VEGF isoforms VEGF121 and VEGF165, receptors VEGFR1, VEGFR2 and co-receptors Neuropilin-1 and Neuropilin-2) 1 and NRP-1, angiopoietin 2, TSP-1 and TSP-2, angiostatin and related molecules, endostatin, vasostatin, calreticulin, platelet factor-4, TIMP and CDAI, Meth-1 and Meth-2, IFN-$\alpha$, -$\beta$ and -$\gamma$, CXCL10, IL-4, -12 and -18, prothrombin (kringle domain-2), antithrombin III fragment, prolactin, VEGI, SPARC, osteopontin, maspin, canstatin, proliferin-related protein, restin and drugs like e.g. bevacizumab, itraconazole, carboxyamidotriazole, TNP-470, CM101, IFN-$\alpha$, platelet factor-4, suramin, SU5416, thrombospondin, VEGFR antagonists, angiostatic steroids+heparin, cartilage-derived angiogenesis Inhibitory factor, matrix metalloproteinase inhibitors, 2-methoxyestradiol, tecogalan, tetrathiomolybdate, thalidomide, thrombospondin, prolactina V$\beta$3 inhibitors, linomide, tasquinimod, For review see Schoenfeld and Dranoff 2011: Anti-angiogenesis immunotherapy. Hum Vaccin. (9):976-81.

10. Small Molecule Targeted Therapy Drugs

Small molecule targeted therapy drugs are generally inhibitors of enzymatic domains on mutated, overexpressed, or otherwise critical proteins within the cancer cell. Prominent and non-limiting examples are the tyrosine kinase inhibitors imatinib (Gleevec/Glivec) and gefitinib (Iressa). The use of small molecules e.g. sunitinib malate and/or sorafenib tosylate targeting some kinases in combination with vaccines for cancer therapy is also described in previous patent application US2009004213.

11. Virus-Based Vaccines

There are a number of virus-based cancer vaccines available or under development which can be used in a combined therapeutic approach together with the formulations of the present invention. One advantage of the use of such viral vectors is their intrinsic ability to initiate immune responses, with inflammatory reactions occurring as a result of the viral infection creating the danger signal necessary for immune activation. An ideal viral vector should be safe and should not introduce an anti-vector immune response to allow for boosting antitumour specific responses. Recombinant viruses such as vaccinia viruses, herpes simplex viruses, adenoviruses, adeno-associated viruses, retroviruses and avipox viruses have been used in animal tumour models and based on their encouraging results, human clinical trials have been initiated. Especially important virus-based vaccines are virus-like particles (VLPs), small particles that contain certain proteins from the outer coat of a virus. Virus-like particles do not contain any genetic material from the virus and cannot cause an infection but they can be constructed to present tumor antigens on their coat. VLPs can be derived from various viruses such as e.g. the hepatitis B virus or other virus families including Parvoviridae (e.g. adeno-associated virus), Retroviridae (e.g. HIV), and Flaviviridae (e.g. Hepatitis C virus). For a general review see Sorensen and Thompsen 2007: Virus-based immunotherapy of cancer: what do we know and where are we going? APMIS 115(11):1177-93; virus-like particles against cancer are reviewed in Buonaguro et al. 2011: Developments in virus-like particle-based vaccines for infectious diseases and cancer. Expert Rev Vaccines 10(11):1569-83; and in Guillen et al. 2010: Virus-like particles as vaccine antigens and adjuvants: application to chronic disease, cancer immunotherapy and infectious disease preventive strategies. Procedia in Vaccinology 2 (2), 128-133.

12. Multi-Epitope Strategies

The use of multi epitopes shows promising results for vaccination. Fast sequencing technologies combined with intelligent algorithms systems allow the exploitation of the tumor mutanome and may provide multi epitopes for individualized vaccines which can be combined with the present invention. For more information see 2007: Vaccination of metastatic colorectal cancer patients with matured dendritic cells loaded with multiple major histocompatibility complex class I peptides. J Immunother 30: 762-772; furthermore Castle et al. 2012: Exploiting the mutanome for tumor vaccination. Cancer Res 72 (5):1081-91.

13. Adoptive T Cell Transfer

For example, a combination of a tumor antigen vaccination and T cell transfer is described in: Rapoport et al. 2011: Combination immunotherapy using adoptive T-cell transfer and tumor antigen vaccination on the basis of hTERT and survivin after ASCT for myeloma. Blood 117(3):788-97.

14. Peptide-Based Target Therapies

Peptides can bind to cell surface receptors or affected extracellular matrix surrounding the tumor. Radionuclides which are attached to these peptides (e.g. RGDs) eventually kill the cancer cell if the nuclide decays in the vicinity of the cell. Especially oligo- or multimers of these binding motifs are of great interest, since this can lead to enhanced tumor specificity and avidity. For non-limiting examples see Yamada 2011: Peptide-based cancer vaccine therapy for prostate cancer, bladder cancer, and malignant glioma. Nihon Rinsho 69(9): 1657-61.

15. Other Therapies

There are numerous other cancer therapies which can be combined with the present invention in order to create synergistic effects. Non-limiting examples are treatments targeting apoptosis, hyperthermia, hormonal therapy, telomerase therapy, insulin potentiation therapy, gene therapy and photodynamic therapy.

The present invention is described in detail by the figures and examples below, which are used only for illustration purposes and are not meant to be limiting. Owing to the description and the examples, further embodiments which are likewise included in the invention are accessible to the skilled worker.

Examples

1. Materials 1,2-di-O-octadecenyl-3-trimethylammonium propane (DOTMA), 1-palmitoyl-2-oleoyl-sn-glycero-3-phosphocholine (POPC), and 1,2-distearoyl-sn-glycero-3-phosphocholine (DSPC) were purchased from Avanti Polar Lipids (Alabaster, Ala.). Cholesterol (purity 99%) was obtained from Sigma (St. Louis, Mo.). Zoledronic acid was obtained from CHEMOS GmbH (Regenstauf, Germany). RNAses free Phosphate buffer saline was purchased from Ambion (Darmstadt, Germany). RNAses free water was purchased from B-Braun (Melsungen, Germany). All of reagents were of analytical grade.

2. Methods

2.1 Liposome Preparation by Ethanol Injection Technique and Further Processing

2.1.1 Preparation of the Liposomes

Liposomes were prepared by a modified ethanol injection technique according to the following protocol:

- 1.5 ml of the aqueous solution of zoledronic acid (3.33 mg/ml) in PBS pH 7.4 was transferred to 50 ml glass beaker. The beaker was put on a magnetic stirrer and the solution was stirred at 400 rpm using IKA big squid model stirrer (IKA, Königswinter Germany).
- 0.55 ml of the lipid/ethanol solution (total lipid concentration 100 mM) was injected by a syringe (Syring type: Omnifix®-F 1 ml sterile plastic syringe, B. Braun; Melsungen, Germany, Needle: fine needle with 27G size) into the zoledronic acid solution under stirring.
- After lipid injection, the suspension was stirred for 10 minutes.
- After 10 minutes, 4 ml of PBS pH 7.4 solution was added to the liposomes. The liposome dispersion was stirred for 20 minutes.

2.1.2 Filtration of the Liposomes

The obtained raw dispersion of the liposomes was passed through a Minisart 0.45 µm CE membrane (Sartorius Stedim Biotech GmbH, Goettingen, Germany).

2.1.3 Dialysis of the Liposomes

Dialysis of the filtered liposomes to remove the free zoledronic acid (non-encapsulated) and ethanol residue was carried out as follows:

Each 1 ml of the liposomes was dialyzed versus 400 ml of PBS by using regenerated cellulose membrane, RNAses free D-tube dialyzer Maxi, MWCO 12-14 KDa (Novagen EMD chemicals Inc., San Diego, Calif., USA). The dialysis took place at room temperature for 24 hrs and at a stirring speed of 400 rpm. The liposomes were recovered in sterile falcon tube for further physicochemical characterizations.

2.2 Liposome Preparation by Reverse-Phase Evaporation Technique and Further Processing

2.2.1 Preparation of the Liposomes

Liposomes were prepared by reverse-phase evaporation technique according to the following protocol:

- 34.02 mg DSPC, 22.32 mg DOPE and 23.70 mg DOEPC were weighed in a round bottom flask.
- Ten ml of chloroform were pipetted into the round bottom flask to dissolve the lipids. Using a rotary evaporator, chloroform was evaporated at 60 rpm and 10 mbar for 1 h.
- The lipid film was redissolved in 3 ml diethyl ether.
- One ml of zoledronic acid solution (10 mg/ml in PBS pH 7.4) was transferred to the diethylether lipid solution and sonicated for about two minutes until a homogenous mixture was obtained.
- The diethylether was removed using a rotary evaporator at 300 mbar and 200 rpm until a homogenous gel was obtained.
- The vacuum was released and the gel flushed with nitrogen gas.
- One ml of PBS was added to the gel.
- The gel was rotated at 200 rpm on the rotary evaporator until a homogenous suspension of liposomes was obtained.
- The liposomes were purged from the diethylether traces by rotation at 60 rpm under high vacuum (200 mbar) for about 2 h.
- The raw dispersion of the liposomes was transferred to a sterile 15 ml Falcon tube.

2.2.2 Filtration of the Liposomes

The obtained raw dispersion of the liposomes was passed through a Minisart 0.40 µm CE membrane (Sartorius Stedim Biotech GmbH, Goettingen, Germany).

2.2.3 Dialysis of the Liposomes

Dialysis of the filtered liposomes to remove the free zoledronic acid (non-encapsulated) and ethanol residue was carried out as follows:

Each 1 ml of the liposomes was dialyzed versus 400 ml of PBS by using regenerated cellulose membrane, RNAses free D-tube dialyzer Maxi, MWCO 12-14 KDa (Novagen EMD chemicals Inc., San Diego, Calif., USA). The dialysis took place at room temperature for 24 hrs and at a stirring speed of 400 rpm. The liposomes were recovered in sterile falcon tube for further physicochemical characterizations.

2.3 Physicochemical Characterization of the Liposomes

2.3.1 Liposome Size, Polydispersity Index (PI), and Zeta-Potential

Liposome size, polydispersity index (PI), and zeta-potential were routinely measured with a Nicomp 380ZLS laser light scattering particle sizer (Santa Barbara, Calif., USA).

2.3.2 Encapsulated and Free Zoledronic Acid (ZA), and Encapsulation Efficiency Determination Encapsulated and free zoledronic acid was quantified by HPLC. The HPLC system consisted of a G1311B quaternary pump, a G4212B DAD (diode array detector) detector, a G1367E auto-sampler AS Hip, a G1330B column oven thermostat, and a ChemStation for LC revision B.04.02 (Agilent technologies, Colorado, USA). The stationary phase was xSelect CSH (C18) column (150 mm×4.6 mm×3.5 µm) (Waters, Eschborn, Germany). The mobile phase was a mixture of methanol (20%) and phosphate buffer 30 mM (80%) containing 5 mM tetrabutylammonium bromide (TCI Deutschland GmbH, Eschborn, Germany) adjusted to pH 7.2. An inoLab pH 7310P pH-meter (WTW, Weilheim, Germany) was used for pH determination of the mobile phase. The flow rate and the column oven temperature were 1 mL/min and 50° C. The detection wavelength was 215 nm. The injection volume amounted to 25 µl. Free zoledronic acid was determined by using high recovery Ultracel with a regenerated cellulose membrane and 30 KD MWCO (Millipore, Schwalbach/Ts., Germany) and using the following steps:

- Removal of any preservatives by filtration of 0.1 M NaOH solution followed by PBS through the membrane.
- Transfer of 500 µl of the liposome sample to 0.5 mL Ultracel tubes.
- Centrifugation of the sample at 14000×g using 40° fixed angle rotor centrifuge Pico 21 (Thermoscientific, Osterode, Germany) at room temperature for 15 minutes.

Collection of the filtrate in a HPLC glass vial for quantification.

Measurement of zoledronic acid concentration in the filtrate by HPLC as mentioned above.

2.3.3 Encapsulation Efficiency % Calculation

Encapsulation efficiency %=[(Total ZA in dialyzed liposomes−Free ZA in dialyzed liposomes/Total ZA in undialyzed liposomes (filtered)]×(100).

2.3.4 Formation of ZARNAsomes

According to the required ratio of cationic lipid/RNA (mole/base), the calculated volume of the ZA-liposomes added to the calculated volume of RNA/PBS. The mixture incubated for at least 15 minutes to form ZARNAsomes.

2.3.5 Determination of Bound RNA/Total RNA in ZARNAsomes

One of the main factors influencing the efficacy of ZARNAsomes is the ratio of bound RNA/free RNA. Therefore, it is prerequisite to know how much of RNA is bound to ZA-liposomes to form ZARNAsomes. Hence, we developed a new method for quantification of bound/total RNA by using bioanalyzing technique. The Agilent's 2100 Bioanalyzer works as follows: Charged biomolecules like DNA or RNA are electrophoretically driven by a voltage gradient similar to slab gel electrophoresis. The molecules are separated by size. Smaller fragments are migrating faster than larger ones. Dye molecules intercalate into DNA or RNA strands or Protein-SDS micelles. These complexes are detected by laser-induced fluorescence. Data are translated into gel-like images (bands) and electropherograms (peaks). With the help of a molecular ladder that contains fragments of known sizes and concentrations, a standard curve of migration time versus fragments size is plotted. From the migration times measured for each fragment in the sample, the size is calculated. In our experiment, ZARNAsomes were prepared by mixing a calculated volume of ZA-liposomes with RNA at nine cationic lipid/RNA charge ratios: Cationic lipid/RNA (mole/base)=0.025, 0.125, 0.25, 0.375, 0.50, 0.625, 0.75, 0.875, 1.00. ZARNAsomes were applied to the bioanalyzer chip and free RNA (unbound to lipid) was calculated from standard calibration curve of pure RNA measured in the same chip with the samples.

2.4 In Vitro Experiments 2.4.1 Cells

Peripheral blood mononuclear cells (PBMCs) were isolated from Buffy Coat donations, drawn from the "Transfusions-Zentrale" of Universitätsmedizin Mainz, by density-centrifugation on a Ficoll-Hypaque density gradient. After isolation PBMCs were further processed to generate CD14 positive mononuclear cells by using CD14 MicroBeads and LS columns (Miltenyi Biotec). Purified CD14 positive cells were used to generate conventional immature dendritic cells (iDCs) by 5-day cultivation in standard medium supplemented with GM-CSF (1000 U/mL) and IL-4 (1000 U/mL). CD14-depleted cells, meaning peripheral blood lymphocytes (PBLs), were frozen in liquid nitrogen to be subsequently used in coculture experiments. The standard medium was RPMI 1640, containing 10% FCS, 2 mM L-glutamine, 100 U/mL penicillin and 100 mg/mL streptomycin.

2.4.2 Flow Cytometry

The following monoclonal antibodies (mAbs) were used: FITC-labeled anti-CD83 (HB15e, BD Pharmingen), PE-labeled anti-CD86 (IT2.2, BD Pharmingen), APC-labeled anti-HLA-DR (G46-6, BD Pharmingen), Pacific Blue-labeled anti-CD3 (UCHT1, BD Pharmingen), FITC-labeled anti-TCR-Vδ2 (B6, BD Pharmingen). Viability of cells was always evaluated by using the fixable viability dye eFluor506 (eBioscience). All flow cytomeric data were acquired using FACSCanto II Flow cytometer (BD Biosciences) and analysed with FlowJo-Software (Tree Star).

2.4.3 Luc-Assay/RNA Expression

To check if the RNA is still intact when it is bound at the outside of the liposomes, the translation of luciferase-encoding RNA was checked by bioluminescence. Here, $2 \times 10^5$ immature dendritic cells (iDCs) were seeded in 96-well plate and incubated as indicated for 24 h. After incubation, samples were centrifuged (300 g, 5 min) and supernatants were discarded. For the luciferase assay system (Bright Glo™, Promega), cell pellets were resuspended in 100 µL standard medium (w/o Pen/Strep) and 1004 assay-substrate solution was added to each well. The luminescence was measured after 10 min incubation with a luminescence reader (Tecan Infinite M200).

2.4.4 Analysis of Dendritic Cell (DC) Maturation

To evaluate whether formulations/substances lead to a maturation of dendritic cells (DCs) after incubation, flow cytometry analysis was performed. Therefore, immature dendritic cells (iDCs) were seeded in standard medium in a 48-well-Plate ($1 \times 10^6$ DCs/mL and well) and incubated as indicated over-night, approximately 20 h. After incubation cells were harvested, washed and stained with anti-CD83, anti-CD86 and anti-HLA-DR mABs. As a positive control for maturation, a so-called "maturation cocktail" containing the following cytokines was used: IL-4 (500 U/mL), GM-CSF (800 U/mL), IL-1β (10 ng/mL), TNF-α (10 ng/mL), IL-6 (1000 U/mL) and PGE-2 (1 µg/mL). For analysis, the expression of these markers has been normalized to negative control, meaning no stimulation (cells only in standard medium).

2.4.5 Vγ9δ2 T Cell Proliferation/Expansion

To check the functionality of the encapsulated compound, zoledronic acid (ZA), the expansion of Vγ9δ2 T cells was evaluated after co-cultivation of ZA-loaded iDCs with cryopreserved PBLs. For evaluation of the ex vivo frequency of Vγ9δ2 T cells, freshly isolated PBMCs were stained with anti-CD3, anti-TCR-Vδ2 mABs and analyzed via flow cytometry. Therefore, iDCs have been incubated as indicated for 24 h in standard medium ($1 \times 10^6$ cells/mL) containing 5 µM ZA. After loading with ZA, iDCs were centrifuged and washed with PBS. The co-culture of iDCs with PBLs was setup in a ratio of 20 (iDCs):1 γ9δ2 T cells ex vivo. The medium was supplemented with 10 U/mL IL-2 (Proleukin). After 7-day incubation, cells were harvested, washed and stained with anti-CD3, anti-TCR-Vδ2 mABs to evaluate frequency of γ9δ2 T cells and their expansion via flow cytometry. For analysis, the expansion rate was determined dividing whole cell amount of γ9δ2 T cells before by after 7-day-cultivation.

2.5 In Vivo Experiments 2.5.1 Animals

Female, 6-12 week old Balb/c mice were obtained from in house breeding of the Zentrale Versuchtiereinrichtung (ZVTE) of the Johannes Gutenberg University Mainz and housed under normal laboratory conditions with circadian light/dark cycles and free access to standard mouse chow and tap water (Approval by the Regional Council's Ethics Committee for Animal Experimentation (Koblenz/Rheinland-Pfalz, Germany, G 12-1-081). Mice were anesthetized with isofluorane and the indicated solutions injected retro-orbital.

2.5.2 RNA Expression Analyzed Via Bioluminescence Imaging

Evaluation of uptake and translation of luciferase (Luc) encoding RNA was performed by non-invasive in vivo bioluminescence imaging using the IVIS Spectrum imaging system (Caliper Life Sciences, Alameda, Calif., USA). 6 h after injection of indicated solutions mice received intraperitoneally an aqueous solution of D-luciferin (150 mg/kg body weight). 5 min later photons emitted were collected for 1 min. Measured bioluminescence signal in regions of interest (ROIs) were quantified and presented as color-scaled images superimposed on grayscale photos of mice using the Living Image software (Caliper Life Sciences). For quantifications, the bioluminescence signal retrieved from the respective organ or tissue was normalized by subtracting background luminescence from a non-signal emitting region.

2.5.3 Splenic DC Maturation Analyzed Via FACS Assay 24 h after injection of indicated solutions, mice were euthanized by cervical dislocation and spleens removed. Splenocytes were obtained by digestion of spleen with collagenase (1 mg/ml; Roche) for 5 min, and subsequently pressing spleens through a 70 μm nylon cell strainer (BD Biosciences, Heidelberg, Germany) using the plunger of a 1 ml syringe. After washing the mesh with PBS, and a centrifugation step for 5 min at 1500 rpm, cells underwent red blood cell lysis (RBC) for 5 min at RT were the pellet was suspended in hypotonically buffer ($KHCO_3/NH_4Cl/EDTA$). And after an additional centrifugation step, cells were suspended in 10 ml PBS/5% FCS. Splenocyte samples were incubated at 4° C. with fluorophore labeled monoclonal antibodies (mAbs) F4-80, CD40, CD86, NK1.1, CD11c, CD8 (all from BD Pharmingen, Heidelberg, Germany) for 30 min, washed with PBS and suspended in 300 μl PBS/5% FCS. Flow cytomeric data of $0.75 \times 10^6$ cells were acquired on a FACSCalibur analytic flow cytometer (BD Biosciences) and analyzed with FlowJo (Tree Star) software.

2.5.4 Test of Isopentenylpyrophosphate (IPP) Accumulation 24 h after injection of indicated solutions, mice were sacrificed and indicated tissue (e.g. spleen) collected. The splenocytes were prepared according to the protocol for the splenic DC maturation measurement by FACS assay, without red blood cell lysis. $5 \times 10^6$ splenocytes were extracted using ice-cold acetonitrile (300 μl) and water (200 μl) containing 0.25 nmol/L NaF and $Na_3VO_4$ to prevent degradation of isopentenylpyrophosphate (IPP) (5 min). After centrifugation at $13.000 \times g$ for 1 min, the soluble supernatant extract was transferred to a fresh Eppendorf tube and dried down in a vacuum centrifuge, then stored at −20° C. until mass spectrometry (MS) analysis of IPP.

2.5.5 Analysis of IPP by Mass Spectrometry

The samples were dissolved in 0.28% (v/v) hexylamine in 2% methanol. The molar amounts of IPP in cell extracts were determined by an Agilent 1290 Infinity UHPLC with a 6490 triple quadrupole mass spectrometer (JetStream Technology, negative ion electrospray ionization). IPP is a very hydrophilic compound and therefore the use of hexylamine as an ion-pair agent was necessary to retain this compound into a reversed-phase column. HPLC separation was performed using a Poroshell 120 EC-C18 column (2.1×50 mm, 2.7 μm) and an eluent system consisting of 2.8% (v/v) hexylamine, 1% acetic acid in methanol (1:50 in water, eluent A) and acetonitrile (eluent B). Flow-rate was 0.4 mL/min and injection volume 20 μL. After HPLC separation, negative ion mass spectra for IPP were acquired using a 6490 triple quadrupole mass spectrometer equipped with an electrospray ionization (ESI) source (Agilent Technologies, Colo., USA). Selected reaction monitoring (SRM) was used for analysis of the compounds in the sample and quantitation was based on characteristic fragment ions. The standard curve was created by using synthetic IPP.

The concentrations of the samples were determined using the peak areas of the SRM chromatograms and the standard curve.

3. Results and Discussion

Figure 1:
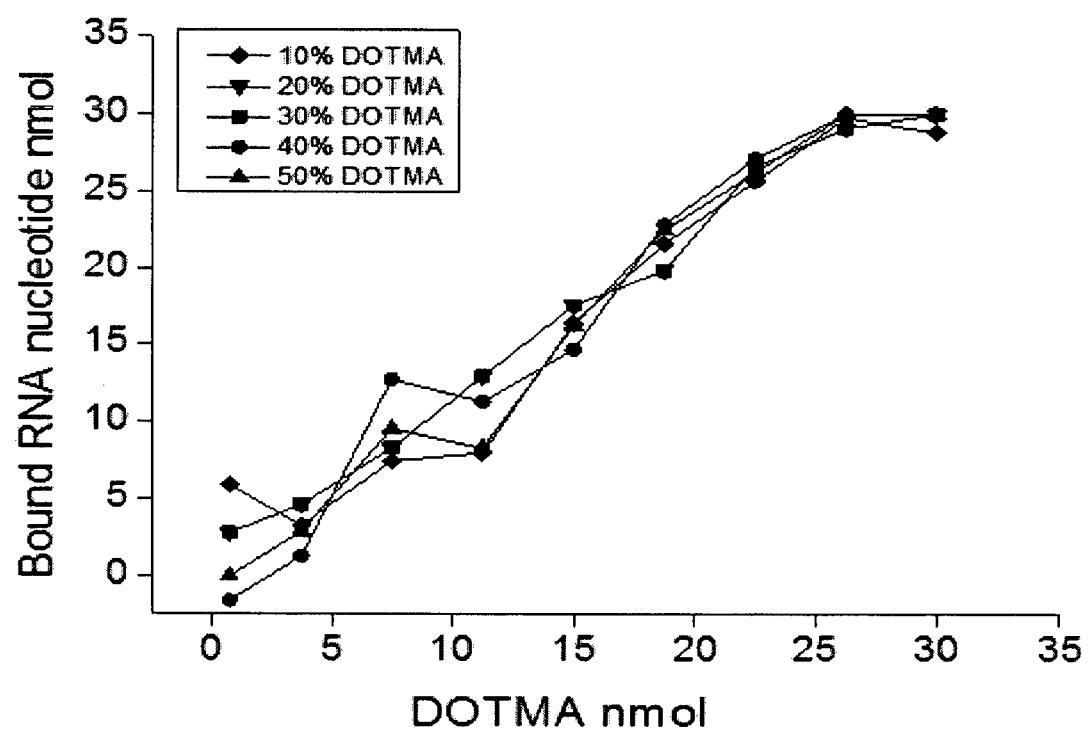
FIG. 1: Binding of RNA as a function of total cationic lipid (DOTMA) in the liposomes.

3.1 Zoledronic Acid (ZA) Encapsulated Liposomes Decorated with RNA for Immunotherapy Zoledronic acid (ZA) encapsulating liposomes (ZA liposomes) with different compositions and molar fractions of the cationic lipid DOTMA were prepared and the binding of RNA to these liposomes was investigated (see FIG. 1). The liposome composition was as follows: DOTMA/CHOL/POPC 10/50/40, DOTMA/CHOL/POPC 20/50/30, DOTMA/CHOL/POPC 30/50/20, DOTMA/CHOL/POPC 40/50/10, and DOTMA/CHOL/POPC 50/50/0 molar ratio, respectively. Thus, the liposomes were composed of 10%, 20%, 30%, 40%, or 50% DOTMA. Binding was investigated by adding an excess of RNA to the zoledronic acid (ZA) encapsulating liposomes (ZA liposomes) and quantifying the RNA by capillary electrophoresis (Bioanalyzer). The DOTMA/RNA charge ratios were as follows: DOTMA/RNA (mole/base)=0.025, 0.125, 0.25, 0.375, 0.50, 0.625, 0.75, 0.875, 1.00. When cationic liposomes were present, the measured amount of RNA decreased. The missing RNA was taken as liposome bound RNA. As can be seen, the amount of bound RNA was directly proportional to the amount of DOTMA present in a one-to-one stoichiometry with respect to the charge. This means, for all tested liposomes, that the amount of bound RNA was directly correlated with the amount of DOTMA in the membrane. As the molar fraction of DOTMA changed (from 10% to 50%), also the amount of bound RNA per liposome and the surface coverage of the liposomes with RNA changed. Thus, in the given experiment, RNA covered liposomes, where the surface coverage with RNA changed by a factor of five, could be assembled in a controlled way. From this experiment, it can be concluded that the amount of RNA decorating the particle of the present invention can be regulated by the amount of cationic lipids, e.g. DOTMA, used. In this way ZA-liposomes with complete or partial RNA surface coverage can be generated.

3.2 Particle Sizes and Polydispersity Indices (PIs) of Cationic ZA-Liposomes after Addition of RNA After having shown that RNA can be bound to ZA-liposomes in a controlled and efficient way, the properties of the RNA-decorated ZA-liposomes such as particle size and polydispersity index (PI) were investigated. The tested liposomes had the following composition: DOTMA/CHOL/POPC 30/50/20, molar ratio. FIG. 2 shows the results of the determination of the particle size and the polydispersity index (PI) of ZA-liposomes comprising the cationic lipid DOTMA and RNA at different charge ratios (i.e. DOTMA/RNA). An excess of negative charges and an excess of positive charges was investigated. In particular, liposomes comprising the cationic lipid DOTMA and RNA, wherein the ratio of DOTMA to RNA was 1/4, 1/2, 1/1, 2/1, and 4/1+/−, were tested. The sizes and polydispersity indices (PIs) of the prepared liposomes were measured by photon correlation spectroscopy. As can be seen in FIG. 2, formulations with discrete particle sizes between 418 and 563 nm were obtained, when an excess of negative charges was present (DOTMA to RNA in a ratio of 1/4 or 1/2) or when the ratio of DOTMA to RNA was 1 to 1. For these charge ratios, no aggregation of the liposomes was observed. The PI of liposomes with an excess of negative charges was comparable with the PI of pure liposomes. Only moderate changes of the particle size with respect to the precursor liposomes occurred (see pure liposomes indicated as "Lipo" in FIG. 2) which may be in line with the bound molecular layer on the liposome surface.

3.3 Particle Size, Polydispersity Index (PI) and Zeta-Potential of ZARNAsomes Prepared by Reverse-Phase Evaporation Technique ZARNAsomes prepared by reverse-phase evaporation technique were also characterized regarding their particle size, polydispersity index (PI) and zeta-potential. They had a size of 390 nm with a polydispersity index (PI) of 0.3. The zeta potential was +41 mV. Using HPLC, concentration of zoledronic acid (ZA) in the liposomes was determined. The zoledronic acid concentration was 0.765 mg/ml, while the concentration of free zoledronic acid was 0.046 mg/ml. Leakage of liposomes inducing release of zoledronic acid could not be observed. This indicates that both, reverse-phase evaporation technique and ethanol injection technique, can be used for preparation of RNA decorated lipid particles (e.g. ZARNAsomes).

3.4 Expression of Luciferase (Luc) In Vitro Transcribed (IVT) RNA in Dendritic Cells (DCs) after Incubation with Liposome Formulations Next, it was tested, whether RNA coding for a protein such as an antigen and bound to ZA-liposomes was still intact and could be translated into a functional protein such as antigen in dendritic cells (DCs). Exemplarily, RNA encoding the enzyme luciferase (Luc) was incubated with ZA-liposomes. The resulting luciferase RNA decorated ZA-liposomes were incubated with dendritic cells, and luciferase expression was evaluated via luminescence indicating the metabolic rate of luciferin being a substrate for luciferase in counts per seconds (cps). FIG. 3 shows the results of the luminescence measurement in dendritic cells incubated with ZA-liposomes (ZA-L) (i.e. zoledronic acid (ZA) encapsulating liposomes), luciferase (Luc) RNA decorated ZA-liposomes (ZARNAsomes) (i.e. luciferase (Luc) RNA decorated zoledronic acid (ZA) encapsulating liposomes) or naked RNA (i.e. luciferase RNA not bound to ZA-liposomes). As can be seen from FIG. 3, only dendritic cells incubated with luciferase RNA decorated ZA-liposomes (ZARNAsomes) showed a luciferase signal. This indicates that dendritic cells could take up ZARNAsomes without destroying the RNA bound to the ZA-liposomes and that the ZARNAsomes were stable enough such that the protein (here luciferase) encoding RNA could be translated. Thus, ZARNAsomes, and accordingly the particles of the present invention, can be used to induce translation of a protein such as an antigen of choice in dendritic cells. This further indicates, that ZARNAsomes, and accordingly the particles of the present invention, can be used for immunotherapy e.g. tumor vaccination.

3.5 Relative Expression of Maturation Markers in Dendritic Cells after Incubation with Liposome Formulations FIG. 4 shows the influence of ZARNAsomes (i.e. RNA decorated zoledronic acid (ZA) encapsulating liposomes) on the maturation of dendritic cells (DCs) in vitro compared to the influence of a positive control (maturation cocktail containing IL-4, GM-CSF, IL-1β, TNF-α, IL-6 and PGE-2), naked RNA and ZA-liposomes (ZA-L) (i.e. zoledronic acid (ZA) encapsulating liposomes). To evaluate the maturation of dendritic cells induced by ZARNAsomes, the relative expression of the maturation markers CD83, CD86 and HLA-DR was determined using flow cytometry. For analysis of the relative expression, the expression of CD83, CD86 and HLA-DR was normalized to the negative control (cells in standard medium). FIG. 4 shows that ZARNAsomes resulted in a distinct higher expression of CD83, CD86 and HLA-DR compared to naked RNA and ZA-liposomes (ZA-L). Regarding CD86 and HLA-DR, the expression induced by ZARNAsomes was even comparable with the positive control. The determined increase of the relative expression induced by ZARNAsomes was between a factor of 1.5 and 3 for CD83, between a factor of 2.0 and 3.5 for CD86 and between a factor of 1.5 and 2.0 for HLA-DR. This indicates that ZARNAsomes induce the maturation of dendritic cells and are, thus, capable of modulating the immune response.

3.6 Functionality of Encapsulated Zoledronic Acid (ZA) after Co-Cultivation of Immature Dendritic Cells (iDCs) Incubated with Liposome Formulations and Peripheral Blood Lymphocytes (PBLs)

Next, it was tested, whether an encapsulated therapeutically agent was still functional after delivery. Therefore, the functionality of zoledronic acid (ZA) delivered by the ZARNAsomes was evaluated. In particular, the capability of zoledronic acid to induce the expansion of Vγ9Vδ2 T cells was tested (Castella, B., Riganti, C., Fiore, F., Pantaleoni, F., Canepari, M. E., Peola, S., Foglietta, M., Palumbo, A., Bosia, A., Coscia, M., Boccadoro, M., Massaia, M. (2011), The Journal of Immunology 187(4), 1578-90). To investigate the influence of ZARNAsomes on the expansion rate of Vγ9Vδ2 cells, zoledronic acid (ZA) loaded immature dendritic cells were co-cultured with peripheral blood lymphocytes containing Vγ9Vδ2 T cells. After seven days of co-culturing, the cells were stained with an anti-CD3 antibody and an anti-TCR-Vδ2 antibody to evaluate the frequency of Vγ9Vδ2 cells and their expansion via flow cytometry. FIG. 5A shows the frequency of Vγ9δ2 T cells regarding all peripheral blood lymphocytes. As it can be seen, ZARNAsomes (i.e. RNA decorated ZA encapsulating liposomes), ZA-liposomes (ZA-L) (i.e. ZA encapsulating liposomes) and free zoledronic acid (ZA) resulted in an increase of the percentage of Vγ9δ2 T cells compared to the negative control (no zoledronic acid (ZA)). FIG. 5B shows the expansion rate of Vγ9δ2 T cells. For analysis, the expansion rate was determined by dividing the whole cell amount of Vγ9δ2 T cells before the seven day cultivation period by the whole cell amount of Vγ9δ2 T cells after the seven day cultivation period. As it can be seen, ZARNAsome treatment resulted in an expansion rate of Vγ9δ2 T cells of about 60-fold, ZA-liposome (ZA-L) treatment resulted in an expansion rate of Vγ9δ2 T cells of about 40-fold and free zoledronic acid (ZA) treatment resulted in an expansion rate of Vγ9δ2 T cells of about 15-fold. Thus, ZARNAsome-induced expansion of Vγ9δ2 T cells is highly efficient indicating both high functionality of the encapsulated zoledronic acid and good delivery properties of the zoledronic acid.

3.7 Application of ZARNAsomes Resulted in Luciferase (Luc) Expression in the Spleen For validation of the in vitro results in vivo, luciferase (Luc) encoding RNA decorated liposomes, corresponding to 20 μg RNA/mouse were injected into Balb/c mice. The translation of luciferase (Luc) RNA bound to liposomes was detected in the presence of luciferin using bioluminescence imaging. FIG. 6A shows that application of ZARNAsomes (i.e. luciferase (Luc) RNA decorated zoledronic acid (ZA) encapsulating liposomes) resulted in luciferase expression in the spleen. FIG. 6A further shows that injection of ZARNAsomes (i.e. Luciferase (Luc) RNA decorated zoledronic acid (ZA) encapsulating liposomes) induced a significant higher luminescence signal than injection of luciferase (Luc) RNA decorated buffer vehicle encapsulating liposomes (EL+Luc-RNA). This indicates that zoledronic acid (ZA) encapsulation does not negatively influence RNA uptake and translation in vivo. It rather enhances the expression of protein such as antigen encoding RNA.

3.8 Application of ZARNAsomes Resulted in an Upregulation of CD40 and CD86 Expression on Splenic Dentric Cells (DCs) and Macrophage (mΦ) Cell Population Further, it was tested whether injection of ZARNAsomes resulted in the maturation of splenic dendritic cells and macrophages in vivo. Therefore, splenocytes of ZARNAsome-treated mices were prepared. Subsequently, the amount of the surface expression of the maturation markers CD40 and CD86 on dendritic cells and macrophages was measured via flow cytometry. FIG. 7 shows that an increase of the signal of CD40 and CD86 compared to the negative control (no treatment) was only detected in dendritic cells and in the macrophage cell population in the presence of Luciferase (Luc) or influenza hemagglutinin A (InfHA) RNA decorated zoledronic acid (ZA) encapsulating liposomes (ZARNAsome Luc-RNA or ZARNAsome infHA-RNA) and Luciferase (Luc) or influenza hemagglutinin A (InfHA) RNA decorated buffer vehicle encapsulating liposomes (EL+Luc-RNA or EL+InfHA-RNA). In contrast thereto, an increase of the signal of CD40 and CD86 compared to the negative control (no treatment) was not detected in dendritic cells and in the macrophage cell population in the presence of undecorated zoledronic acid (ZA) encapsulating liposomes (ZA-L), buffer vehicle encapsulating liposomes (EL) or free RNAs (free Luc-RNA or free InfHA-RNA). These results indicate that treatment with RNA-decorated liposomes induces maturation of dendritic cells and macrophages in vivo. As luciferase encoding RNA (Luc-RNA) as well as influenza hemagglutinin A encoding RNA (InfHA-RNA) induced maturation of dendritic cells and macrophages, the induction of maturation appears to be independent from the encoded protein. Therefore, any RNA can be used for decorating the particles of the present invention in order to induce maturation of splenic dendritic cells and macrophages. This provides a useful method in order to generally induce maturation of splenic dendritic cells and macrophages as well as to introduce an antigen into splenic dendritic cells and macrophages which is specifically useful for vaccination or other immunotherapeutic approaches.

3.9 Application of Carboxyfluorescin (CF)—Filled Liposomes Decorated with Luc-RNA (CF-Filled ZARNAsome) Leads to Transfection of Splenic Cell Populations where Dendritic Cells (DCs) and Macrophages (mΦ) are the Main Target Next, it was analyzed, whether the RNA decorated liposomes were taken up by splenic dendritic cells, macrophages, B cells or T cells. To monitor the uptake of RNA decorated liposomes, liposomes filled with the dye carboxyfluorescin (CF) and decorated with Luciferase (Luc) RNA were injected into mice. One hour after injection, splenocytes were prepared and analyzed using FACS analysis. FIG. 8 shows that injection of carboxyfluorescin-filled liposomes decorated with luciferase RNA (CF-filled ZARNAsome) in mice resulted in an uptake of said liposomes in splenic dendritic cells, macrophages, B cells and T cells, whereby dendritic cells and macrophages were the main targets. This indicates that the RNA decorated lipid particles of the present invention preferably target antigen presenting cells such as dendritic cells and macrophages. Thus, the RNA decorated lipid particles of the present invention can be used for introducing RNA and therapeutic effective agents into dendritic cells and macrophages. In addition, dendritic cells and macrophages can be used for antigen presentation as well as for immune response induction/modulation.

3.10 Zoledronic Acid Leads to Accumulation of Isopentenylpyrophosphate (IPP) in the Spleen After having shown that RNA provided by the ZARNAsomes is functionally active, the function of zoledronic acid encapsulated in the ZARNAsome was tested in vivo. Zoledronic acid has been shown to induce accumulation of isopentenylpyrophosphate (IPP) in various cell lines in vitro and tumor tissue in vivo and could be directly related to improved clinical outcome of cancer of different origin. (Mitrofan, L. M., Pelkonen, J., Mönkkönen, J., (2009), Bone, 45, 1153-60). Thus, IPP accumulation in the spleen was investigated after injection of the liposome formulations using mass spectrometry. FIG. 9 shows that the treatment with undecorated zoledronic acid (ZA) encapsulating liposomes (ZA-L) and luciferase (Luc) RNA decorated zoledronic acid (ZA) encapsulating liposomes (ZARNAsomes Luc-RNA) resulted in a significant increase of the IPP concentration in the spleen compared to the negative control (no treatment), free luciferase (Luc) RNA (free RNA), buffer vehicle encapsulating liposomes (EL) and buffer vehicle encapsulating liposomes decorated with luciferase (Luc) encoding RNA (EL+Luc-RNA). This indicates that zoledronic acid delivered by ZARNAsomes is still functional after delivery in vivo. Thus, the in vivo data confirmed the results of the in vitro data, indicating that RNA decorated lipid particles such as ZARNAsomes can be used for drug delivery.

In summary, it is shown by means of ZARNAsomes that RNA decorated lipid particles are useful for introduction of protein such as antigen encoding RNA as well as for drug delivery in order to induce/modulate the immune response in an individual.

ABBREVIATIONS

ZA=Zoledronic acid
ZA-L=zoledronic acid encapsulating liposome
ZARNAsome=RNA decorated zoledronic acid encapsulating liposome
ZARNAsome Luc RNA=Luc RNA decorated zoledronic acid encapsulating liposome
ZARNAsome infHA RNA=infHA RNA decorated zoledronic acid encapsulating liposome
EL=buffer vehicle encapsulating liposome
EL+RNA=RNA decorated buffer vehicle encapsulating liposome
EL+Luc RNA=Luc RNA decorated buffer vehicle encapsulating liposome
EL+infHA RNA=infHA RNA decorated buffer vehicle encapsulating liposome
Luc=Luciferase
infHA=influenza hemagglutinin A
CF=carboxyfluorescein
IPP=Isopentenylpyrophosphate
DOTMA=1,2-di-O-octadecenyl-3-trimethylammonium propane
CHOL=Cholesterol
POPC=1-palmitoyl-2-oleoyl-sn-glycero-3-phosphocholine
PI=polydispersity index
$Z_{ave}$=Z-average
i.v.=intra venous
DC=dentritic cell
iDC=immature dendritic cell
PBMCs=peripheral blood mononuclear cells PBLs=peripheral blood lymphocytes
mΦ=macrophage
MFI=mean fluorescence intensity
Cntr=control

The invention claimed is:

1. A particle comprising:
   (i) a vesicular core,
   (ii) at least one therapeutically effective compound encapsulated within the vesicular core, and
   (iii) RNA forming a hydrophilic shell on at least a portion of the vesicular core,
   wherein the RNA encodes at least one pharmaceutically active peptide or protein, and
   wherein the RNA encodes at least one antigen, wherein the antigen is a disease-associated antigen or elicits an immune response against a disease-associated antigen or cells expressing a disease-associated antigen, wherein the disease-associated antigen is a tumor antigen, a viral antigen, or a bacterial antigen.

2. The particle of claim 1, wherein the therapeutically effective compound is a water-soluble compound that is sparingly soluble (i.e., the approximate volume of water in milliliters per gram of solute is from 30 to 100 (at a temperature between 15° C. and 25° C.)), soluble (i.e., the approximate volume of water in milliliters per gram of solute is from 10 to 30 (at a temperature between 15° C. and 25° C.)), freely soluble, (i.e., the approximate volume of water in milliliters per gram of solute is from 1 to 10 (at a temperature between 15° C. and 25° C.)), or very soluble (i.e., the approximate volume of water in milliliters per gram of solute is less than 1 (at a temperature between 15° C. and 25° C.)).

3. The particle of claim 1, wherein the therapeutically effective compound is an agent stimulating γδ T cells.

4. The particle of claim 3, wherein the agent stimulating γδ T cells is a bisphosphonate.

5. The particle of claim 3, wherein the agent stimulating γδ T cells is selected from the group consisting of zoledronic acid, clodronic acid, ibandronic acid, pamidronic acid, risedronic acid, minodronic acid, olpadronic acid, alendronic acid, incadronic acid and salts thereof.

6. The particle of claim 3, wherein the agent stimulating γδ T cells is an aminobisphosphonate.

7. The particle of claim 1, wherein the vesicular core is positively charged.

8. The particle of claim 1, wherein the vesicular core is a polymer vesicular core, a protein vesicular core or a lipid vesicular core.

9. The particle of claim 8, wherein the lipid vesicular core comprises a lipid bilayer.

10. The particle of claim 8, wherein the lipid vesicular core comprises a liposome.

11. The particle of claim 8, wherein the lipid vesicular core comprises at least one cationic lipid.

12. The particle of claim 11, wherein the at least one cationic lipid comprises 1,2-dimyristoyl-sn-glycero-3-ethylphosphocholine (DMEPC), 1,2-di-O-octadecenyl-3-trimethylammonium propane (DOTMA) and/or 1,2-dioleoyl-3-trimethylammonium propane (DOTAP).

13. The particle of claim 8, wherein the lipid vesicular core comprises at least one helper lipid.

14. The particle of claim 13, wherein the helper lipid is a neutral lipid or negatively charged lipid.

15. The particle of claim 13, wherein the at least one helper lipid comprises 1,2-distearoyl-sn-glycero-3-phosphocholine (DSPC), 1,2-di-(9Z-octadecenoyl)-sn-glycero-3-phosphoethanolamine (DOPE), cholesterol (Chol), 1-palmitoyl-2-oleoyl-sn-glycero-3-phosphocholin (POPC) and/or 1,2-dioleoyl-sn-glycero-3-phosphocholine (DOPC).

16. The particle of claim 1, wherein the particle has an average diameter in the range of from about 50 nm to about 1000 nm.

17. A pharmaceutical composition comprising a particle according to claim 1 and one or more pharmaceutically acceptable carriers, diluents, and/or excipients.

18. The particle of claim 1, wherein the therapeutically effective compound is an agent stimulating Vγ9Vδ2 T cells.

19. The particle of claim 1, wherein the vesicular core is a lipid vesicular core.

20. A particle comprising:
   (i) a vesicular core,
   (ii) at least one therapeutically effective compound encapsulated within the vesicular core, and
   (iii) RNA forming a hydrophilic shell on at least a portion of the vesicular core,
   wherein the RNA is in vitro transcribed mRNA which encodes at least one pharmaceutically active peptide or protein.

* * * * *

UNITED STATES PATENT AND TRADEMARK OFFICE
CERTIFICATE OF CORRECTION

PATENT NO. : 9,950,065 B2  
APPLICATION NO. : 15/023052  
DATED : April 24, 2018  
INVENTOR(S) : Ugur Sahin et al.

Page 1 of 1

It is certified that error appears in the above-identified patent and that said Letters Patent is hereby corrected as shown below:

On the Title Page

At item (72) Inventors:
Please delete "Hossam Hefresha, Wiesbaden (DE)" and replace it with --Hossam Hefesha, Wiesbaden (DE)--.

Signed and Sealed this
Twenty-third Day of October, 2018

Andrei Iancu
*Director of the United States Patent and Trademark Office*